United States Patent [19]
Bacon et al.

[11] Patent Number: 5,958,929
[45] Date of Patent: *Sep. 28, 1999

[54] 6-ARYL PYRAZOLO [3,4-D] PYRIMIDIN-4-ONES AND COMPOSITIONS AND METHODS OF USE THEREOF

[75] Inventors: Edward R. Bacon, Audubon; Baldev Singh, Collegeville, both of Pa.

[73] Assignee: Sanofi, France

[*] Notice: This patent is subject to a terminal disclaimer.

[21] Appl. No.: 09/016,572

[22] Filed: Jan. 30, 1998

Related U.S. Application Data

[62] Division of application No. 08/788,893, Jan. 22, 1997, Pat. No. 5,736,548, which is a continuation of application No. 08/402,261, Mar. 10, 1995, abandoned.

[51] Int. Cl.$^6$ ........................ A61K 31/505; C07D 487/04
[52] U.S. Cl. ........................ 514/258; 514/212; 514/228.5; 514/234.2; 544/58.6; 544/118; 544/262; 540/600
[58] Field of Search ...................... 544/58.6, 118, 544/262; 540/600; 514/212, 228.5, 234.2, 258

[56] References Cited

U.S. PATENT DOCUMENTS

| | | | |
|---|---|---|---|
| 3,165,520 | 1/1965 | Schmidt et al. | 260/256.4 |
| 3,211,731 | 10/1965 | Schmidt et al. | 260/256.4 |
| 3,211,732 | 10/1965 | Schmidt et al. | 260/256.4 |
| 3,732,225 | 5/1973 | Breuer et al. | 260/256.4 |
| 3,772,294 | 11/1973 | Podesva et al. | 260/256.4 |
| 4,666,908 | 5/1987 | Hamilton | 514/229 |
| 5,075,310 | 12/1991 | Coates et al. | 514/258 |
| 5,294,612 | 3/1994 | Bacon et al. | 514/234.2 |

FOREIGN PATENT DOCUMENTS

| | | |
|---|---|---|
| 0463756 | 1/1992 | European Pat. Off. . |
| 636626 | 2/1995 | European Pat. Off. . |
| 937722 | 9/1963 | United Kingdom . |
| 88/00192 | 1/1988 | WIPO . |
| 93/07149 | 4/1993 | WIPO . |

OTHER PUBLICATIONS

Miyashita et al., Heterocycles, 1990, 31, 1309–1314.

Dumaitre et al., J. Med. Chem., 1996, 39, 1635–1644.

*Primary Examiner*—Mukund J. Shah
*Assistant Examiner*—Ann M. Kessinger
*Attorney, Agent, or Firm*—Michael D. Alexander

[57] ABSTRACT

6-Aryl pyrazolo[3,4-d]pyrimidin-4-one derivatives, pharmaceutical compositions containing them and methods for effecting c-GMP-phosphodiesterase inhibition and for treating heart failure and/or hypertension.

24 Claims, No Drawings

6-ARYL PYRAZOLO [3,4-D] PYRIMIDIN-4-ONES AND COMPOSITIONS AND METHODS OF USE THEREOF

CROSS-REFERENCE TO RELATED APPLICATIONS

This application is a division of our prior application Ser. No. 08/788,893, filed Jan. 22, 1997, now U.S. Pat. No. 5,736,548, which in turn is a continuation of our prior application Ser. No. 08/402,261, filed Mar. 10, 1995, now abandoned.

BACKGROUND OF THE INVENTION (a) Field of the Invention

The invention relates to 6-aryl pyrazolo[3,4-d]-pyrimidin-4-ones, to pharmaceutical compositions containing them and to methods for effecting c-GMP-phosphodiesterase inhibition and for treating heart failure and/or hypertension.

(b) Information Disclosure Statement

Schmidt et al., U.S. Pat. No. 3,165,520, issued Jan. 12, 1965, disclose as coronary dilating agents pyrazolo[3,4-d] pyrimidines of general formula:

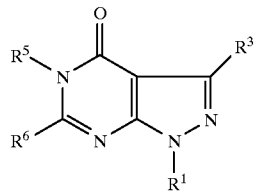

wherein:

$R^1$ represents a hydrogen atom or an alkyl, hydroxyalkyl, halogen-alkyl or oxa-alkyl radical or a cycloalkyl, cycloalkylalkyl, aralkyl or heterocyclylalkyl radical or an at most binuclear aryl or heterocyclic radical;

$R^3$ represents a hydrogen atom or a lower-alkyl radical;

$R^5$ represents an aliphatic, cycloaliphatic, cycloaliphatic-aliphatic, araliphatic or heterocyclic-aliphatic radical; and $R^6$ represents an aliphatic radical or an aralkyl or heterocyclyl-alkyl radical which may be substituted.

The patent more specifically discloses as especially valuable the compounds in which $R^1$ represents a hydrogen atom or a lower-alkyl radical or a cycloalkyl radical, a hydroxy-lower-alkyl radical or halogen-lower-alkyl radical, an oxa-lower-alkyl, or an aryl radical which may be unsubstituted or mono-, di-, or tri-substituted by halogen, alkoxy, alkyl, methylenedioxy, trifluoromethyl, nitro, amino, or a pyridyl radical; $R^3$ represents a hydrogen atom or a lower-alkyl radical; $R^5$ represents a lower-alkyl radical or a lower-alkylamino radical; and $R^6$ represents a lower-alkyl radical or an aralkyl radical.

Further disclosed are a series of 1-$R^1$-3-$R^3$-4-hydroxy-6-$R^6$-pyrazolo[3,4-d]pyrimidines which are said to be useful as intermediates in the synthesis of final products. Among the intermediates specifically disclosed are 1-cyclopentyl-4-hydroxy-6-benzyl-pyrazolo[3,4-d]pyrimidine and 1-isopropyl-4-hydroxy-6-m-methoxybenzylpyrazolo[3,4-d] pyrimidine.

Schmidt et al., U.S. Pat. No. 3,211,731, issued Oct. 12, 1965, disclose as coronary dilating agents pyrazolo[3,4-d] pyrimidines of general formula:

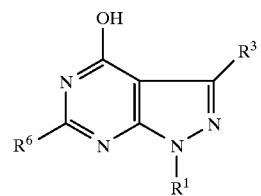

wherein:

$R^1$ represents hydrogen, an alkyl, hydroxy-alkyl, halogen-alkyl or oxa-alkyl radical, a cyclo-alkyl, cyclo-alkylalkyl, aralkyl, heterocyclyl-alkyl radical or an at most binuclear aryl or heterocyclic radical;

$R^3$ stands for hydrogen, or in the second place, for a lower-alkyl radical; and $R^6$ represents a possibly substituted aralkyl or heterocyclylalkyl radical.

The patent more specifically discloses as especially valuable the compounds in which $R^1$ represents a hydrogen atom or a lower-alkyl group, cycloalkyl, hydroxy-lower-alkyl, halogen-lower-alkyl, oxa-lower-alkyl, or an aryl; $R^3$ represents a hydrogen atom or lower-alkyl and $R^6$ a substituted or unsubstituted aralkyl. Among the compounds specifically disclosed are 1-isopropyl-4-hydroxy-6-(3'-methoxyphenylmethyl)pyrazolo[3,4-d]pyrimidine, 1-cyclopentyl-4-hydroxy-6-benzylpyrazolo[3,4-d] pyrimidine, 1-isopropyl-4-hydroxy-6-(β-phenylethyl) pyrazolo[3,4-d]pyrimidine, and 1-isopropyl-4-hydroxy-6-(4-aminobenzyl)pyrazolo[3,4-d]pyrimidine.

Schmidt et al., U.S. Pat. No. 3,211,732, issued Oct. 12, 1965, disclose, as intermediates, 1-$R^1$-3-$R^3$-6-$R^6$-4-hydroxy-pyrazolo[3,4-d]pyrimidines wherein:

$R^1$ represents a hydrogen atom, a lower-alkyl radical which is unsubstituted or substituted by a hydroxy group or a lower-alkoxy group, or a cyclopentyl or cyclohexyl radical or a phenyl or phenyl lower-alkyl radical;

$R^3$ represents a hydrogen atom or a lower-alkyl radical; and $R^6$ stands for a substituted or unsubstituted phenyl lower-alkyl radical.

Specifically disclosed is 1-isopropyl-4-hydroxy-6-benzylpyrazolo[3,4-d]pyrimidine.

Also disclosed, as intermediates, are 1-$R^1$-3-$R^3$-6-$R^6$-4-hydroxypyrazolo[3,4-d]pyrimidines wherein:

$R^1$ stands for a hydrogen atom, a lower-alkoxy-lower-alkyl radical or a hydroxy-lower-alkyl radical, a cyclopentyl or cyclohexyl radical or a phenyl or phenyl-lower-alkyl radical which may be substituted;

$R^3$ has the meanings given above; and $R^6$ stands for a phenyl radical which may be substituted. Specifically disclosed is 1-isopropyl-4-hydroxy-6-phenylpyrazolo[3,4-d]pyrimidine.

Breuer et al., U.S. Pat. No. 3,732,225, issued May 8, 1973, disclose as hypoglycemic agents and anti-inflammatory agents pyrazolo[3,4-d]pyrimidines of formula:

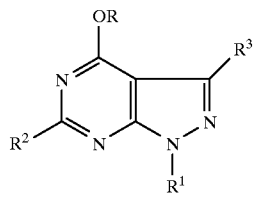

wherein:

R is hydrogen or lower-alkyl; R¹ is lower-alkyl, cycloalkyl, phenyl or substituted phenyl; R² is phenyl, substituted phenyl or cycloalkyl; and R³ is hydrogen, lower-alkyl, cycloalkyl, phenyl or substituted phenyl. Specifically disclosed are 1-methyl-6-phenyl and 1-methyl-6-(4-chlorophenyl)pyrazolo[3,4-d]pyrimidin-4-ones.

British Patent 937,722, published Sep. 25, 1963, to CIBA LIMITED, discloses as a coronary dilating agent 1-isopropyl-4-hydroxy-6-benzyl-pyrazolo[3,4-d] pyrimidine.

Hamilton, U.S. Pat. No. 4,666,908, issued May 19, 1987, discloses pyrazolo[4,3-d]pyrimidine-7-ones of formula:

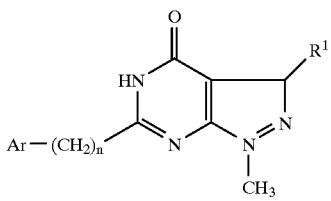

wherein:

R¹ is lower-alkyl of from one to six carbons, inclusive, lower-alkylene of from one to six carbon, inclusive, lower-hydroxyalkyl of from one to six carbons, inclusive, lower-hydroxyalkylene of from two to six carbons, inclusive, lower-aminoalkyl of from one to six carbons, inclusive, or lower-aminoalkylene of from two to six carbons, inclusive;

n is 0–4; and

Ar is R₂:

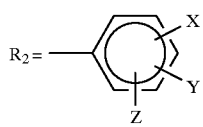

or 2, 3 or 4-pyridyl wherein X, Y and Z are independently (1) hydrogen; (2) lower-alkyl of from one to six carbons, inclusive; (3) halogen; (4) hydroxyl; (5) lower-alkoxy of from one to six carbons, inclusive; (6) nitro; (7) amino; (8) NR'R" wherein R' and R" are each independently (a) hydrogen or (b) lower-alkyl of from one to six carbons, inclusive, optionally substituted by (i) amino, (ii) morpholino, or (iii) cycloalkyl of from five to seven carbons, inclusive, (9) sulfonyl or (10) —SO2 NR'R" wherein R' and R" are as defined above.

The patent more specifically discloses as preferred compounds those wherein Ar is R₂. The compounds are stated to be useful in the treatment of cardiovascular disorders.

Miyashita et al., Heterocycles 1990, 31, 1309–1314, describe the preparation of a series of pyrazolo[3,4-d] pyrimidines of general formula:

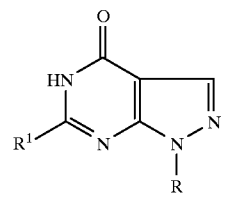

wherein:

R is phenyl or methyl; and R¹ is hydrogen, methyl, ethyl, propyl, isopropyl, benzyl, ethyl carboxylate or phenyl. No indication of utility is disclosed.

Hamilton, PCT Application WO 88/00192, published Jan. 14, 1988, discloses a series of 5-substituted pyrazolo[4,3-d] pyrimidin-7-one derivatives which are stated to be useful as cardiotonic, CNS stimulative, antiallergy, antiasthma or cognition activating agents.

Bell et al., European Patent Application 0463756, published Jan. 2, 1992, disclose a series of 5-(2,5-disubstituted-phenyl)pyrazolo[4,3-d]pyrimidin-7-ones which are stated to be useful in the treatment of cardiovascular disorders.

Podesva et al., U.S. Pat. No. 3,772,294, issued Nov. 13, 1973, disclose a process for preparing compounds of the formula I:

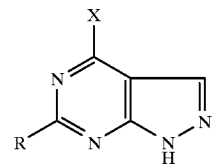

wherein:

X represents a halogen atom, a free or substituted hydroxyl, amino or mercapto group and R represents a hydrogen atom, or a lower-alkyl or a substituted or unsubstituted aryl radical. The compounds are disclosed as being potentially useful in the treatment of hyperuricemia associated with gout and other conditions and additionally, the compounds wherein X represents a halogen atom are said to be useful as intermediates in the synthesis of other compounds having the formula I. Specifically disclosed is 4-hydroxy-6-phenyl-1-pyrazolo[3,4-d]pyrimidine.

Coates and Rawlings, U.S. Pat. No. 5,075,310, issued Dec. 24, 1991 from application Ser. No. 370,494 filed Jun. 23, 1989, disclose and claim compounds of the formula:

and pharmaceutically acceptable salts thereof, wherein:

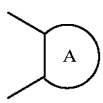

is a ring of sub-formula (a), (b) or (c):

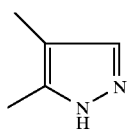
(a)

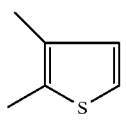
(b)

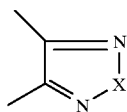
(c)

X is oxygen or sulphur; and $R^1$ is $C_1$-$C_6$ alkyl, $C_{2-6}$ alkenyl, $C_{3-5}$ cycloalkyl-$C_{1-4}$ alkyl, or $C_{1-4}$ alkyl substituted by 1 to 6 fluoro groups. Specifically disclosed is 6-(2-propoxyphenyl)pyrazolo[3,4-d]pyrimidin-4(5H)-one. The compounds are said to be useful as bronchodilators and vasodilators.

Bacon et al, U.S. Pat. No. 5,294,612 issued Mar. 15, 1994 from application Ser. No. 859,770 filed Mar. 30, 1992, discloses a series of 6-heterocyclyl-pyrazolo[3,4-d]pyrimidin-4-ones, e.g., 1-cyclopentyl-3-ethyl-6-(3-pyridyl)pyrazolo[3,4-d]pyrimidin-4-one. The compounds are disclosed to be useful in treating heart failure and hypertension.

SUMMARY OF THE INVENTION

The invention relates to compounds of the Formula I:

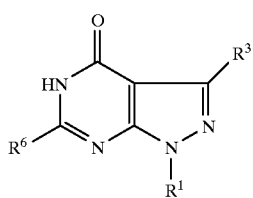
I wherein:

$R^1$ is tert-butyl, or cyclopentyl;

$R^3$ is lower-alkyl, or phenyl-lower-alkyl; and $R^6$ is phenyl, or phenyl substituted by from one to three, the same or different, substituents selected from the group consisting of lower-alkoxy, lower-alkyl, hydroxy, 1-imidazolyl, lower-alkenyloxy, dilower-alkylamino-lower-alkoxy, 4-morpholinyl-lower-alkoxy, lower-alkoxycarbonyl-lower-alkoxy, carboxylower-alkoxy, trifluoromethyl, 1-piperidinyl-lower-alkoxy, 1-pyrrolidinyl-lower-alkoxy, nitro, halo, amino, —(CH$_2$)$_2$O—, lower-alkylsulfonylamino, lower-alkoxy-lower-alkoxy, lower-alkenyl, dilower-alkylamino, —OCH(CH$_3$)CH$_2$—, 4-morpholinylcarbonyl-lower-alkoxy, 4-thiomorpholinyl-lower-alkoxy, pyridinyl-lower-alkoxy, 1-lower-alkyl-3-hexahydroazepinyloxy, and 1-lower-alkyl-4-piperidinyl oxy; or a pharmaceutically acceptable acid-addition salt and/or hydrate thereof.

The compounds of the Formula I have been found to possess c-GmP-PDE V inhibitory activity and are thus useful in the treatment of heart failure and/or hypertension.

Preferred compounds of Formula I above are those wherein $R^1$ is cyclopentyl; $R^3$ is methyl or ethyl; and $R^6$ is as defined hereinabove.

Particularly preferred compounds of Formula I above are those wherein:

$R^1$ is cyclopentyl;

$R^3$ is methyl, or ethyl; and $R^6$ is phenyl, or phenyl substituted by from one to two, the same or different, substituents selected from the group consisting of methoxy, ethoxy, propoxy, methyl, hydroxy, 1-imidazolyl, CH$_2$=CHCH$_2$O—, 2-(dimethylamino)ethoxy, 3-(dimethylamino)propoxy, 2-(4-morpholinyl)ethoxy, 3-(4-morpholinyl)propoxy, ethoxycarbonyl methoxy, carboxymethoxy, trifluoromethyl, 2-(1-piperidinyl)ethoxy, 2-(1-pyrrolidinyl)ethoxy, nitro, chloro, amino, —(CH$_2$)$_2$O—, methylsulfonylamino, 2-(methoxy)ethoxy, CH$_2$=CH$_2$CH$_2$—, diethylamino, —OCH(CH$_3$)CH$_2$—, 4-morpholinyl-carbonylmethoxy, 2-(4-thiomorpholinyl)ethoxy, 4-pyridinylmethoxy, 1-methyl-3-hexahydroazepinyloxy, and 1-methyl-4-piperidinyloxy.

Particularly preferred species of the invention are:

1-cyclopentyl-3-ethyl-6-(2-propoxyphenyl)pyrazolo[3,4-d]pyrimindin-4-one, 1-cyclopentyl-3-ethyl-6-[4-(1-imidazolyl)phenyl]pyrazolo[3,4-d]pyrimindin-4-one, 1-cyclopentyl-3-ethyl-6-[3-(2-(4-morpholinyl)ethoxy)phenyl]pyrazolo[3,4-d]pyrimindin-4-one, 1-cyclopentyl-3-ethyl-6-[2-ethoxy-4-(1-imidazolyl)phenyl]pyrazolo[3,4-d]pyrimindin-4-one, and 1-cyclopentyl-3-ethyl-6-[2-(CH$_2$=CHCH$_2$O)phenyl]pyrazolo[3,4-d]pyrimindin-4-one.

The invention further relates to pharmaceutical compositions which comprise compounds of Formula I together with a pharmaceutically acceptable carrier, adjuvant, diluent, or vehicle.

The invention further relates to a method for effecting cGMP-phosphodiesterase inhibition in a mammalian organism which comprises administering to said organism an effective amount of a compound of Formula I.

The invention further relates to a method for treating heart failure and/or hypertension in a mammalian organism which comprises administering to said organism an effective amount of a compound of the Formula I.

DETAILED DESCRIPTION INCLUSIVE OF PREFERRED EMBODIMENTS

The compounds of Formula I may exist in tautomeric equilibrium with the corresponding enol form:

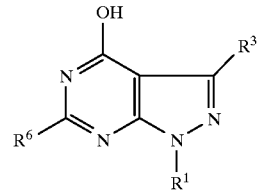

While the compounds are believed to be predominantly in the keto form and will be represented as such throughout this specification, it is to be understood that the invention contemplates both forms and mixtures thereof.

The term lower-alkyl as used herein means linear or branched hydrocarbon chains having from one to about four carbon atoms and thus includes methyl, ethyl, propyl, isopropyl, n-butyl, sec-butyl, and the like.

The term lower-alkoxy as used herein means linear or branched alkyloxy substituents having from one to about four carbon atoms and thus includes methoxy, ethoxy, propoxy, isopropoxy, butoxy, sec-butoxy, and the like.

The term halogen, halide, or halo as used herein means bromine, chlorine, iodine or fluorine.

The term lower-alkenyl as used herein means branched or unbranched unsaturated hydrocarbon radicals of from two to about four carbon atoms and thus includes 1-ethenyl, 1-propenyl, 2-propenyl, 1-methyl-2-propenyl, isopropenyl, 2-butenyl, isobutenyl, and the like.

The synthesis of compounds of the invention may be outlined as shown in Scheme A:

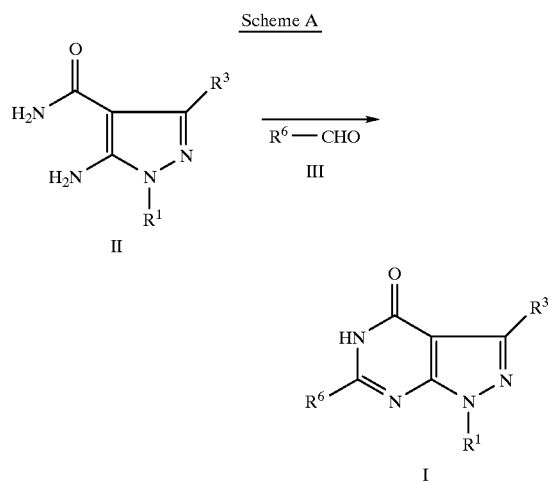

A suitably substituted 5-amino-1H-pyrazolo-4-carboxamide (II) is reacted with an excess of an appropriately substituted aldehyde of the formula III, optionally in the presence of a suitable organic solvent, preferably xylenes, or benzene, with or without the use of an acid catalyst, preferably p-toluenesulfonic acid, acetic acid, or methanesulfonic acid, optionally in the presence of palladium on carbon, at a temperature in the range of about room temperature up to the boiling point of the reaction mixture, preferably at the boiling point of the reaction mixture, to afford the compounds of the formula I.

Alternatively, a suitably substituted 5-amino-1H-pyrazole-4-carboxamide (II) is treated with an excess of an ester of the formula IV: $R^6C(O)OR$ wherein R is lower-alkyl, preferably ethyl, in the presence of a base, preferably sodium ethoxide, in an alcoholic solvent, such as ethanol, at a temperature in the range of about room temperature up to the boiling point of the solvent used, preferably at the boiling point of the solvent used, to afford the compounds of the formula I.

The compounds of the formula I can also be synthesized as shown in Scheme B:

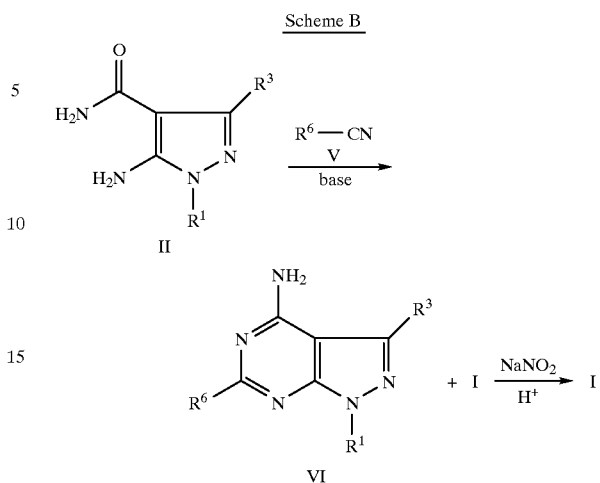

A suitably substituted 5-amino-1H-pyrazole-4-carboxamide of the formula II is treated with an excess of a nitrile of the formula V in a suitable organic solvent, preferably dimethylformamide (DMF), or dioxane, in the presence of an excess of a suitable base, preferably sodium hydride, at a temperature in the range of about room temperature up to the boiling point of the solvent used, to afford either the compounds of the formula I directly, or a mixture of the compounds of the formula I and the pyrazolo[3,4-d] pyrimidin-4-amines of the formula VI. This mixture can in turn be treated with an excess of sodium nitrite, in a 1/1 water/acid mixture, preferably a 1/1 water/sulfuric acid mixture, at a temperature in the range of about −10° C. up to about room temperature to afford the compounds of the formula I.

Simple chemical transformations which are conventional and well known to those skilled in the art of chemistry can be used for effecting changes in the fuctional groups of the compounds of the formula I. For example, dealkylation of aryl ethers to afford the corresponding phenol derivatives, hydrolysis of esters to afford the corresponding acids, catalytic reduction of nitro derivatives to afford the corresponding amines, and sulfonylation of amines to afford the corresponding sulfonamide derivatives.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The appropriately substituted 5-amino-1H-pyrazole-4-carboxamides of the formula II are either known and thus can be prepared by known procedures (see, for example, U.S. Pat. No. 5,294,612, issued Mar. 15, 1994, the entire contents of which is incorporated herein by reference), or they can be prepared by the procedures described hereinbelow in the examples. The aldehydes of the formula III, the esters of the formula IV and the nitriles of the formula V are either commercially available, or they can be prepared by procedures known in the art, or by the procedures described hereinbelow in the examples.

The structures of the compounds of the invention were established by the mode of synthesis, and by one or more of elemental analysis, and infrared, nuclear magnetic resonance and mass spectroscopy. The course of the reactions and the identity and homogenity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (°C.) and are uncorrected.

EXAMPLE 1

(a)

A solution of salicylaldehyde (12.21 g, 0.1 mol) in DMF (65 ml) was cooled in an ice/water bath under argon and 60% sodium hydride in mineral oil (4.0 g, 0.1 mol) was added in several portions. The mixture was stirred for one hour and then iodopropane (16.99 g, 0.1 mol) was added at room temperature. The reaction mixture was stirred at room temperature overnight, poured into water (800 ml) and stirred. The mixture was extracted with chloroform (3×), the chloroform layer was concentrated in vacuo and the dark oil thus obtained was distilled under vacuum (92–94° C. at 1.15 mm Hg) to afford 12.68 g (77%) of 2-propoxybenzaldehyde.

(b)

A solution of KOH (12.16 g, 184.2 mmol) in water (150 ml) was cooled in an ice-bath and then 1-cyclopentyl-3-methyl-5-amino-1H-pyrazole-4-carbonitrile (5.0 g, 26.3 mmol), followed by 30% hydrogen peroxide (13.5 ml, 131.6 mmol) were added. The reaction mixture was warmed to room temperature and stirred overnight. A precipitate formed which was collected by filtration and washed with ether to afford 1-cyclopentyl-3-methyl-5-amino-1H-pyrazole-4-carboxamide, as a white solid. Additional product was obtained by concentration of the filtrate and collection of the product by filtration to afford a total of 4.46 g of product.

Alternatively, the carboxamide was prepared as follows: A solution of concentrated sulfuric acid (50 ml) was cooled to −5° C. and 1-cyclopentyl-3-methyl-5-amino-1H-pyrazole-4-carbonitrile (2.0 g, 10.5 mmol) was added. The mixture was stirred as such for 2 hours, then at room temperature overnight. The reaction mixture was poured into 400 ml of ice and NH$_4$OH (100 ml) and was stirred for 1 hour. The product precipitated and was collected by filtration. Additional product was obtained by acidifying the filtrate with acetic acid to a pH of 5 and then extracting with chloroform. The chloroform layers were concentrated in vacuo and titurated with ether to afford, after filtration and drying at 100° C. overnight, 1.67 g (76%) of 1-cyclopentyl-3-methyl-5-amino-1H-pyrazole-4-carboxamide, m.p. 191–192° C.

(c)

A mixture of 1-cyclopentyl-3-methyl-5-amino-1H-pyrazole-4-carboxamide (3.98 g, 0.019 mol), 2-propoxybenzaldehyde (6.35 g, 0.038 mol), xylenes (150 ml) and methanesulfonic acid (0.5 ml) was heated at reflux for 39 hours with azeotropic removal of water. The reaction mixture was concentrated in vacuo and the residue was treated with 10% K$_2$CO$_3$ and ether. The layers were separated, the aqueous layer was extracted with ether and the combined ether layers were concentrated in vacuo. Analysis of the reaction mixture by TLC indicated that the reaction was not yet complete, therefore, the mixture was heated at 180° C. on an oil bath. The residue was dissolved in chloroform, and purified by column chromatography on silica gel eluting with hexane (100%) followed by ether (100%) to afford 2.67 g (41%) of 1-cyclopentyl-3-methyl-6-(2-propoxyphenyl)-pyrazolo[3,4-d]pyrimidin-4-one, m.p. 130–132° C.

Alternatively, the final product was prepared as follows: A mixture of 1-cyclopentyl-3-methyl-5-amino-1H-pyrazole-4-carboxamide (1.0 g, 4.8 mmol) and 2-propoxybenzaldehyde (10.6 g, 10 mmol) was heated at 160° C. on an oil bath for 4 hours then at 170° C. for 48 hours. The reaction mixture was cooled, chloroform (5 ml) was added and the solution was eluted on a silica gel column with ether (100%) to afford, after recrystallization from cyclohexane, 0.16 g of 1-cyclopentyl-3-methyl-6-(2-propoxyphenyl)pyrazolo[3,4-d]pyrimidin-4-one.

EXAMPLE 2

A mixture of 1-cyclopentyl-3-ethyl-5-(4-quinolinyl-CH=N—)1H-pyrazole-4-carboxamide (6.34 g, 0.018 mol), benzaldehyde (0.96 g, 0.009 mol), xylenes (150 ml) and methanesulfonic acid (0.5 ml) was refluxed overnight. The reaction mixture was concentrated in vacuo, and the residue was treated with ethanol (200 ml) and azeotroped. The residue was then treated with 10% K$_2$CO$_3$ (100 ml), titurated with ether, filtered and washed with water. The product was recrystallized from ethyl acetate and dried at 100° C. to afford 2.68 g of crude product which was purified by column chromatography on silica gel to afford 0.603 g of 1-cyclopentyl-3-ethyl-6-phenyl-pyrazolo[3,4-d]pyrimidin-4-one, m.p. 221–222° C.

Alternatively, and preferably, the final product can be prepared from 1-cyclopentyl-3-ethyl-5-amino-1H-pyrazole-4-carboxamide and benzaldehyde following a procedure similar to that described in example 1 (c).

EXAMPLE 3

A mixture of 1-cyclopentyl-3-ethyl-5-amino-1H-pyrazole-4-carboxamide (2.0 g, 9 mmol), o-tolualdehyde (2.16 g, 18 mmol), methanesulfonic acid (0.5 ml) and xylenes (50 ml) was refluxed for 32 hours. The solvent was removed and the residue was treated with ethanol (100 ml) and then concentrated to dryness. The dark residue was treated with 10% $K_2CO_3$ and chloroform, the organic layer was separated and the aqueous layer was extracted with chloroform (2×100 ml). The organic layers were combined, concentrated to approximately 20 ml and then added to silica gel (30 g). The preloaded silica gel was placed on a silica gel column and eluted with $Et_2O$/hexanes (2/8) to (5/5) to afford, after drying at 70° C. in vacuo, 1.10 g (40%) of 1-cyclopentyl-3-ethyl-6-(2-methylphenyl)-pyrazolo[3,4-d]pyrimidin-4-one, m.p. 133–134° C.

EXAMPLE 4

A mixture of 1-cyclopentyl-3-ethyl-5-amino-1H-pyrazole-4-carboxamide (2.0 g, 9 mmol), o-ethoxybenzaldehyde (2.7 g, 18 mmol), methanesulfonic acid (5 drops), and xylenes (50 ml) was refluxed for 48 hours. The reaction mixture was stripped to dryness, and treated with 10% $K_2CO_3$ and $CHCl_3$ (100 ml). The layers were separated and the aqueous layer was extracted with chloroform (2×100 ml). The organic layers were combined, and concentrated in vacuo. The dark oil thus obtained was dissolved in $CH_2Cl_2$ (30 ml) and combined with silica gel (30 g). The preloaded silica gel was placed on a silica gel column and eluted with $Et_2O$/hexanes (20/80) to $Et_2O$ (100%) to afford 1.41 g (45%) of 1-cyclopentyl-3-ethyl-6-(2-ethoxyphenyl)-pyrazolo[3,4-d]pyrimidin-4-one, m.p. 146–147° C.

EXAMPLE 5

A mixture of 1-cyclopentyl-3-ethyl-5-amino-1H-pyrazole-4-carboxamide (2.0 g, 9 mmol), anisaldehyde (2.45 g, 18 mmol), xylenes (50 ml) and p-toluenesulfonic acid (0.5 g) was refluxed for 32 hours. The reaction mixture was stripped to dryness, treated with ethanol (100 ml) and then again concentrated to dryness. The residue was treated with $CHCl_3$ (100 ml) and 10% $K_2CO_3$ (100 ml), the layers were separated and the aqueous layer was extracted with chloroform (3×100 ml). The combined organic layers were concentrated to approximately 25 ml and then combined with silica gel (30 g). The preloaded silica was placed on a silica gel column and eluted with ether/hexanes (8/10) to ether (100%) to afford 1.25 g (41%) of 1-cyclopentyl-3-ethyl-6-(2-methoxyphenyl)-pyrazolo[3,4-d]pyrimidin-4-one, m.p. 135–136° C., after recrystallization from cyclohexane.

EXAMPLE 6

A mixture of 1-cyclopentyl-3-ethyl-5-amino-1H-pyrazole-4-carboxamide (1.0 g, 4.5 mmol), 2-propoxybenzaldehyde (1.5 g, 9 mmol), p-toluenesulfonic acid (0.5 g) and xylenes (50 ml) was refluxed for 20 hours. The reaction mixture was stripped to dryness, treated with ethanol and again concentrated to dryness. The residue was treated with $CHCl_3$ (100 ml) and washed with saturated $NaHCO_3$. The organic layer was concentrated to a dark oil which was dissolved in $CH_2Cl_2$ (30 ml) and combined with silica gel (50 g). The preloaded silica gel was placed on a silica gel column and eluted with 10% hexanes/ether to ether (100%) to afford, after crystallization from hexanes, 0.492 g (30%) of 1-cyclopentyl-3-ethyl-6-(2-propoxyphenyl)-pyrazolo[3,4-d]pyrimidin-4-one, m.p. 93–94° C.

EXAMPLE 7

To a solution of 1-cyclopentyl-3-ethyl-6-(2-methoxyphenyl)-pyrazolo[3,4-d]pyrimidin-4-one (0.5 g, 1.5 mmol) in DMF (10 ml) was added NaH (0.15 g, 3.75 mmol, 60% NaH in mineral oil). The reaction mixture was stirred for 20 minutes, then propanethiol (0.228 g, 3.0 mmol) was added and the mixture was stirred at room temperature for 4 hours, then at 110° C. for 9 hours. The reaction mixture was stripped to dryness and then water (15 ml) followed by acetic acid (1 ml) were added. A precipitate formed which was collected by filtration, washed with water and recrystallized by DARCO® treatment from ethyl acetate to afford 0.28 g (58%) of 1-cyclopentyl-3-ethyl-6-(2-hydroxyphenyl)-pyrazolo[3,4-d]pyrimidin-4-one, m.p. 272–273° C., as white fibrous needles.

EXAMPLE 8

(a)

A mixture of 1-cyclopentyl-3-ethyl-5-amino-1H-pyrazole-4-carboxamide (1.18 g, 5.32 mmol), 4-(1-imidazolyl)benzaldehyde (1.37 g) and xylenes (8 ml) was warmed to 130° C. for 30 minutes, then to 160° C. for three days. The reaction mixture was cooled, and the product was collected by filtration and washed with $Et_2O$ to afford 1.88 g of 1-cyclopentyl-3-ethyl-6-[4-(1-imidazolyl)phenyl]pyrazolo[3,4-d]pyrimidin-4-one as the 6,7-saturated derivative. This derivative was mixed with ethanol (300 ml) and 30% $H_2O_2$ (3.0 ml) and refluxed overnight. Additional 30% $H_2O_2$ (3 ml) was added and the mixture was refluxed for 8 hours. An additional 10 ml of 30% $H_2O_2$ was added and the mixture was refluxed overnight. Starting material was still present so an additional 10 ml of 30% $H_2O_2$ was added and the mixture was refluxed for 4 hours and then additional 30% $H_2O_2$ (10 ml) was added and the mixture was stirred for 1 hour, then was allowed to stand at room temperature overnight. The reaction mixture was stripped to a yellow liquid and purified by column chromatography on silica gel eluting with ethyl acetate (100%), then 5% methanol/ethyl acetate to afford 0.4 g of 1-cyclopentyl-3-ethyl-6-[4-(1-imidazolyl)phenyl]-pyrazolo[3,4-d]pyrimidin-4-one ½ hydrate, m.p. >300° C.

(b)

Alternatively, the product can be obtained as follows:

To a mixture of imidazole (5.13 g, 75.35 mmol), $K_2CO_3$ (11.45 g) and DMSO (50 ml) at room temperature was added to 4-fluorobenzonitrile (10.04 g) in one portion. The reaction mixture was stirred at room temperature for 1 hour, and then was warmed on a steam for 2 hours. The reaction mixture was cooled to room temperature, and poured into cold water. A precipitate formed which was collected by filtration and washed with water and recrystallized from $CHCl_3$/hexane to afford 4.07 g of 4-(1-imidazolyl)benzonitrile, m.p. 146–148° C.

To a mixture of 4-(1-imidazolyl)benzonitrile (0.9 g, 5.27 mmol), 1-cyclopentyl-3-ethyl-5-amino-1H-pyrazole-4-carboxamide (1.17 g) in DMF (20 ml) at room temperature was added NaH (0.63 g, 60% dispersion in mineral oil). The reaction mixture was stirred at room temperature overnight, additional NaH (0.5 g) was added and the mixture was stirred at room temperature for about 2 days. The reaction mixture was poured into ice/water (500 ml), neutralized with acetic acid and the precipitate which formed was collected by filtration, washed with hexanes, dissolved in $CHCl_3$, dried over $MgSO_4$, filtered and concentrated in vacuo. The residue was recrystallized from ethyl acetate, combined with the product obtained from two similar experimental runs and then recrystallized from $CH_3CN/CHCl_3$ to afford 1-cyclopentyl-3-ethyl-6-[4-(1-imidazolyl)phenyl]pyrazole [3,4-d]pyrimidin-4-one, m.p. >300° C.

EXAMPLE 9

(a)

To a solution of ethyl salicylate (100 g, 0.602 mol) in DMF (400 ml) was added $K_2CO_3$ (150 g), followed by the dropwise addition of allyl bromide (87.5 g, 0.723 mol). The reaction mixture was then heated on a steam bath for 2 hours, the $K_2CO_3$ was removed by filtration and the reaction mixture was poured into water and extracted with ethyl acetate (3×300 ml). The organic layer was washed with brine, and dried over $MgSO_4$, and the solvent was removed to afford 122 g (98%) of ethyl 2-(2-propenyloxy)benzoate.

(b)

Sodium spheres (207 mg) was dissolved in ethanol (15 ml) and 1-cyclopentyl-3-ethyl-5-amino-1H-pyrazole-4-carboxamide (1 g, 45 mmol) was added, followed by ethyl 2-(2-propenyloxy)benzoate (1.85 g, 9 mmol). The reaction mixture was refluxed overnight, cooled, the ethanol was stripped and water was added. The pH was adjusted to about 7 and a solid was isolated by filtration. The solid was taken up in ether, washed with dilute HCl, dried over $MgSO_4$, filtered and the solvent was removed and the solid residue was recrystallized from ether to afford 0.56 g of 1-cyclopentyl-3-ethyl-6-[2-($CH_2$=CH—$CH_2O$)phenyl] pyrazolo[3,4-d]pyrimidin-4-one, m.p. 119–120° C.

EXAMPLE 10

A mixture of 1-cyclopentyl-3-ethyl-5-amino-1H-pyrazole-4-carboxamide (2.03 g, 9.14 mmol), 4-[3-(dimethylamino)propoxy]benzaldehyde (2.76 ml), and xylenes was heated at 120° C. for 1 hour, then at 160° C. for 6 hours. p-Toluenesulfonic acid (300 mg) was added and the mixture was heated at 160° C. until the reaction was complete. The reaction mixture was cooled to room temperature, and a creamy white solid formed, which was collected by filtration, washed with methanol and recrystallized from ethyl acetate to afford 1-cyclopentyl-3-ethyl-6-[4-[3-(dimethylamino)propoxy]phenyl]pyrazolo[3,4-d] pyrimidin-4-one, as a white solid, m.p. 175–178° C.

EXAMPLE 11

(a)

To a solution of salicylaldehyde (2 ml) in acetonitrile (20 ml) was added $K_2CO_3$ (5.71 g), followed by N-(2-chloroethyl)morpholine hydrochloride (3.5 g) and then the mixture was stirred at room temperature for 2 hours, then at reflux overnight. The reaction mixture was cooled to room temperature, filtered, and the filtrate was concentrated in vacuo to afford 2-[2-(4-morpholinyl)ethoxy]benzaldehyde, as a yellow oil.

(b)+(c)

A mixture of 1-cyclopentyl-3-ethyl-5-amino-1H-pyrazole-4-carboxamide (0.95 g, 4.28 mmol), 2-[2-(4-morpholinyl)ethoxy]benzaldehyde (1.51 g) and xylenes (15 ml) was heated to 120° C. for 1 hour, then to 160° C. until the reaction was complete. The reaction mixture was then cooled to room temperature, the solvent was removed in vacuo, and the residue was purified by silica gel chromatography eluting with ethyl acetate (100%), followed by ethanol/ethyl acetate (1/1) to afford 1-cyclopentyl-3-ethyl-6-[2-[2-(4-morpholinyl)ethoxy]phenyl]pyrazolo[3,4-d] pyrimidin-4-one (Example 11 (b)), as an oil. The free base was then converted into its hydrochloride salt, which was recrystallized from ethanol and dried at 110° C. under high vacuum to afford 0.5 g of 1-cyclopentyl-3-ethyl-6-[2-[2-(4-morpholinyl)ethoxy]phenyl]pyrazolo[3,4-d]pyrimidin-4-one monohydrochloride, as an off-white powder, m.p. 235–237° C., labelled as Example 11 (c).

EXAMPLE 12

(a)

A mixture of 2-formylphenoxyacetic acid (9.01 g, 0.05 mol), ethanol (4.6 g), concentrated $H_2SO_4$ (0.4 ml) and toluene (40 ml) was heated to reflux with azeotropic removal of water for 1 hour. The reaction mixture was poured into 10% $KHCO_3$ (100 ml), the layers were separated and the aqueous layer was extracted with ether (2×75 ml). The organic layers were combined, and concentrated in vacuo to afford 9.1 g (95%) of 2-(ethoxycarbonylmethoxy) benzaldehyde.

(b)

A mixture of 1-cyclopentyl-3-ethyl-5-amino-1H-pyrazole-4-carboxamide (5.26 g, 23.7 mmol), 2-(ethoxycarbonylmethoxy)benzaldehyde (9.10 g, 47.3 mmol), p-toluenesulfonic acid (0.2 g) and xylenes (100 ml) was refluxed for 18 hours with the azeotropic removal of water. The solvent was removed in vacuo, and the residue was treated with ethanol and evaporated to dryness. The residue was partitioned between chloroform and 10% aqueous $K_2CO_3$, the layers were separated and the aqueous layer was extracted with chloroform (100 ml). The organic layers were combined, and concentrated to dryness. The residue was preloaded on silica gel and then was purified by column chromatography on silica gel eluting with hexanes (100%) to 20% ether/hexane to afford 3.74 g (38%) of 1-cyclopentyl-3-ethyl-6-[2-(ethoxycarbonylmethoxy) phenyl]pyrazolo[3,4-d]pyrimidin-4-one, m.p. 116–117° C.

EXAMPLE 13

(a)

To a solution of 3-Hydroxybenzaldehyde (3.05 g, 24.97 mmol) in acetonitrile (15 ml) was added $K_2CO_3$ (7.6 g), followed by N-(2-chloroethyl)morpholine hydrochloride (4.65 g). The reaction mixture was stirred at room temperature for 30 minutes, then at reflux overnight. Additional N-(2-chloroethyl)morpholine hydrochloride (0.93 g) and $K_2CO_3$ (0.7 g) were added and the mixture was refluxed for an additional 6 hours. The reaction mixture was cooled to room temperature, filtered and the filtrate was concentrated in vacuo. The residue was partitioned between water and chloroform, the layers were separated and the aqueous layer was extracted with chloroform (2×75 ml). The organic layers were combined, washed with brine, dried over $MgSO_4$, filtered and stripped to afford 7.3 g of 3-[2-(4-morpholinyl)ethoxy]benzaldehyde, as an amber liquid.

(b)

A mixture of 1-cyclopentyl-3-ethyl-5-amino-1H-pyrazole-4-carboxamide (1.05 g, 4.73 mmol), 3-[2-(4-morpholinyl)ethoxy]benzaldehyde (1.67 g) and xylenes (7 ml) was heated to 160° C. overnight. Additional aldehyde (0.4 g) was added and the mixture was heated at 160° C.

until the reaction was complete. The reaction mixture was cooled to room temperature and a solid formed which was collected by filtration and washed with ether. The filtrate was concentrated to dryness and the residue was combined with the solid and was purified by column chromatography on silica gel eluting with ethyl acetate/ethanol (60/40). The solid product thus obtained was washed with ether, recrystallized from ethyl acetate and then washed with ether again to afford 1-cyclopentyl-3-ethyl-6-[3-[2-(4-morpholinyl) ethoxy]phenyl]-pyrazolo[3,4-d]pyrimidin-4-one, m.p. 173–176° C.

EXAMPLE 14

A mixture of 1-cyclopentyl-3-ethyl-5-amino-1H-pyrazole-4-carboxamide (1.19 g, 5.38 mmol), 2-methoxy-4-carboxymethoxybenzaldehyde (1.13 g) and glacial acetic acid (25 ml) was warmed to reflux for 4 days. The reaction mixture was cooled to room temperature and the solvent was stripped to afford a slurry which was washed with methanol, collected by filtration and then washed with ether. The product was recrystallized from ethanol and washed with ether to afford 1-cyclopentyl-3-ethyl-6-[(2-methoxy-4-carboxymethoxy)phenyl]pyrazolo[3,4-d]pyrimidin-4-one.

EXAMPLE 15

A mixture of 1-cyclopentyl-3-ethyl-5-amino-1H-pyrazole-4-carboxamide (0.59 g, 2.65 mmol), 2-trifluoromethylbenzaldehyde (0.5 ml) and glacial acetic acid (25 ml) was refluxed overnight and then 0.5 equivalents of additional aldehyde was added and the mixture was refluxed for about 3 days. The reaction mixture was cooled to room temperature, the acetic acid was stripped and the residue was cooled and rinsed with ether to give a white solid which was collected by filtration and recrystallized from tert-butyl dimethyl ether/hexanes to afford 1-cyclopentyl-3-ethyl-6-(2-trifluoromethylphenyl)-pyrazolo [3,4-d]pyrimidin-4-one, m.p. 201–202° C.

EXAMPLE 16

A mixture of 1-cyclopentyl-3-ethyl-6-[2-(ethoxycarbonylmethoxy)pheny]pyrazolo[3,4-d]pyrimidin-4-one (3.0 g, 7.3 mmol), $K_2CO_3$ (3.04 g), water (20 ml) and ethanol (50 ml) was refluxed for 1.5 hours. The reaction mixture was cooled, the solvent was removed in vacuo and the residue was slurried with water and acidified. A precipitate formed which was collected by filtration, recrystallized from isopropanol and dried at 90° C. The solid was dissolved in 10% $K_2CO_3$ (100 ml), treated with DARCO®, filtered and the filtrate was acidified with acetic acid. A precipitate formed which was collected by filtration and dried at 110° C. The solid product was combined with the solid product obtained from a similar experimental run, stirred with 6N HCL (100 ml), filtered and dried with $P_2O_5$ at 100° C. under vacuum to afford 2.09 g of 1-cyclopentyl-3-ethyl-6-[2-(carboxymethoxy)phenyl]pyrazolo[3,4-d] pyrimidin-4-one ½ hydrate, m.p. 208–209° C.

EXAMPLE 17

(a)

To a mixture of water (500 ml) and 85% KOH (37.91 g) at 0° C. was added 30% $H_2O_2$ (49.4 ml, 483 mmol), followed by 1-tert-butyl-5-amino-1H-pyrazole-4-carbonitrile (15.83 g, 96.5 mmol). The reaction mixture was stirred for four hours at 0° C. and then at room temperature for 1 hour. A yellow precipitate had formed which was collected by filtration and air dried to afford 13.2 g (75%) of 1-tert-butyl-5-amino-1H-pyrazole-4-carboxamide, m.p. 193–195° C.

(b)

A mixture of 2-propoxybenzaldehyde (3.0 g, 18.27 mmol), 1-tert-butyl-5-amino-1H-pyrazole-4-carboxamide (2.5 g, 13.7 mmol), methanesulfonic acid (0.2 ml) and xylenes (50 ml) was refluxed overnight. The reaction mixture was stripped to dryness, treated with ethanol and again stripped to dryness. The residue was partitioned between chloroform and 10% $KHCO_3$, the layers were separated, and the aqueous layer was extracted with chloroform (2×100 ml). The organic layers were combined, and concentrated in vacuo and the residue was dissolved in $CH_2Cl_2$ (30 ml) and combined with silica gel (20 g). The preloaded silica gel was placed on a silica gel column and eluted with 70% ether/hexanes, followed by ether (100%) to afford 0.98 g (22%) of 1-tert-butyl-6-(2-propoxyphenyl)pyrazolo[3,4-d]pyrimidin-4-one ¹⁄₁₀₀ hydrate, m.p. 130–131° C.

(c)

A mixture of 1-tert-butyl-6-(2-propoxyphenyl)pyrazolo [3,4-d]pyrimidin-4-one ¹⁄₁₀₀ hydrate (0.68 g, 2.1 mmol) and trifluoroacetic acid (50 ml) was heated on a steam bath for 3.5 hours. The reaction mixture was stripped to dryness and the residue was purified by column chromatography on silica gel eluting with ether to afford 0.45 g (79%) of 6-(2-propoxyphenyl)pyrazolo[3,4-d]pyrimidin-4-one.¼ hydrate, m.p. 170–171° C.

EXAMPLE 18

(a)

To a solution of 4-hydroxybenzaldehyde (4.04 g, 33.08 mmol), in acetonitrile (50 ml) was added $K_2CO_3$ (10.1 g), followed by N-(2-chloroethyl)morpholine hydrochloride (6.16 g). The reaction mixture was heated to reflux overnight, additional N-(2-chloroethyl)morpholine hydrochloride (0.6 g) and $K_2CO_3$ (0.5 g) were added and the mixture was refluxed for another 3 hours. The reaction mixture was cooled to room temperature, filtered, and the filtrate was treated with DARCO®, filtered and the solvent was stripped. The residue was partitioned between saturated $NaHCO_3$ (150 ml) and ethyl acetate (300 ml). The layers were separated and the organic layer was washed with 1N NaOH, dried over $MgSO_4$, filtered and stripped to afford, as an amber oil, 6.41 g of 4-[2-(4-morpholinyl)ethoxy] benzaldehyde.

(b)

A mixture of 1-cyclopentyl-3-ethyl-5-amino-1H-pyrazole-4-carboxamide (2.19 g, 9.86 mmol), 4-[2-(4-morpholinyl)ethoxy]benzaldehyde (3.5 g) and xylenes (10 ml) was heated at 160° C. overnight. p-Toluenesulfonic acid (0.2 g) was added and the mixture was heated at 160° C. overnight. The reaction mixture was cooled to room temperature, and the precipitate which formed was slurried with methanol, collected by filtration and washed with methanol, and then ether. The product was recrystallized from acetonitrile to afford 1-cyclopentyl-3-ethyl-6-[4-[2-(4-morpholinyl)ethoxy]phenyl]pyrazolo[3,4-d]pyrimidin-4-one.

EXAMPLE 19

(a)

To a mixture of 3-hydroxybenzaldehyde (5.42 g, 44.38 mmol), $K_2CO_3$ (13.5 g) and acetonitrile was added N-(2- chloroethyl)piperidine hydrochloride (9.8 g). The reaction mixture was refluxed overnight, cooled to room temperature and filtered. The filtrate was stripped to give an oil which was partitioned between CHCl₃ (350 ml) and 1M NaOH (200 ml). The organic layer was separated, washed with 1M NaOH (2×200 ml), treated with DARCO®, then MgSO₄, filtered, and stripped to afford, as a dark oily liquid, 6.28 g of 3-[2-(1-piperdinyl)ethoxy]benzaldehyde.

(b)

A mixture of 1-cyclopentyl-3-ethyl-5-amino-1H-pyrazole-4-carboxamide (2.02 g, 9.09 mmol), 3-[2-(1-piperidinyl)]ethoxy]benzaldehyde (3.18 g) and xylenes (10 ml) was refluxed overnight. Additional aldehyde (0.5 g) was added and the mixture was heated at 160° C. for 6 hours. The reaction was still not complete so an additional 0.5 g of aldehyde was added and the mixture was refluxed for about 2 days. The reaction mixture was cooled, filtered and stripped to afford an oily residue. The residue was treated with acetonitrile and chilled and the precipitate which formed was collected by filtration and washed with ether. The product was purified by column chromatography on silica gel eluting with ethyl acetate/hexanes (1/1), followed by recrystallization from acetonitrile to afford, as a white solid, 1-cyclopentyl-3-ethyl-6-[3-[2-(1-piperidinyl)ethoxy]phenyl]pyrazolo[3,4-d]pyrimidin-4-one, m.p. 180° C.

EXAMPLE 20

(a)

To a mixture of 3-hydroxybenzaldehyde (5.17 g, 42.34 mmol), K₂CO₃ (5.85 g) and acetone (50 ml) was added ethyl bromoacetate (5.2 ml). The reaction mixture was stirred at room temperature overnight, additional K₂CO₃ (1 equivalent) was added, the mixture was stirred for one hour, then additional ethyl bromoacetate (0.5 equivalents) was added and the mixture was stirred at room temperature until the reaction was complete. The reaction mixture was filtered, water was added to the filtrate and the solvent was removed. The residue was dissolved in ether, extracted with 1M NaOH (2×100 ml), and the ether layer was dried over MgSO₄ and stripped to afford, as a liquid, 7.89 g of 3-(ethoxycarbonylmethoxy)benzaldehyde.

(b)

A mixture of 1-cyclopentyl-3-ethyl-5-amino-1H-pyrazole-4-carboxamide (3.54 g, 15.95 mmol), 3-(ethoxycarbonylmethoxy)benzaldehyde (4.3 g) and xylenes (20 ml) was heated at 160° C. overnight. The reaction mixture was cooled to room temperature, a solid formed which was collected by filtration and washed with methanol and then ether. The product was recrystallized from acetonitrile to afford 2.48 g of 1-cyclopentyl-3-ethyl-6-[3-(ethoxycarbonylmethoxy)phenyl]pyrazolo[3 4-d]pyrimidin-4-one. An additional 0.3 g of product was also obtained from the recrystallization of the filtrate for a total of 2.78 g.

EXAMPLE 21

To a slurry of 1-cyclopentyl-3-ethyl-6-[3-(ethoxycarbonylmethoxy)phenyl]pyrazolo[3,4-d]pyrimidin-4-one (1.23 g, 3.0 mmol) in ethanol (10 ml) was added water (100 ml), followed by 85% KOH (0.4 g). The reaction mixture was heated on a steam bath for 3 hours, cooled to room temperature and filtered. The filtrate was chilled and acidified with acetic acid to afford a white precipitate, which was collected by filtration and washed with water, then ethanol, and finally ether. The product was combined with the product from another experimental run and then was recrystallized from DMF/CH₃CN to afford 0.98 g of 1-cyclopentyl-3-ethyl-6-[3-(carboxymethoxy)phenyl]pyrazolo[3,4-d]pyrimidin-4-one, m.p. 299–300° C.

EXAMPLE 22

(a)

To a mixture of 3-hydroxybenzaldehyde (4.15 g, 33.98 mmol), KOH (4.93 g) and DMSO (50 ml) was added N-(2-chloroethyl)pyrrolidine hydrochloride (6.94 g). The reaction mixture was stirred at room temperature overnight, then was poured into water (750 ml) and ethyl acetate (350 ml) was added. The layers were separated, the aqueous layer was extracted with ethyl acetate and the combined organic layers were washed with water (2×1000 ml), dried over MgSO₄, filtered and stripped to afford 7.12 g of 3-[2-(1-pyrrolidinyl)ethoxy]benzaldehyde.

(b)

A mixture of 1-cyclopentyl-3-ethyl-5-amino-1H-pyrazolo-4-carboxamide (2.32 g, 10.45 mmol), 3-[2-(1-pyrrolidinyl)ethoxy]benzaldeyde (2.98 g), and xylenes (10 ml) was heated at 160° C. overnight. Additional aldehyde (0.5 g), and p-toluenesulfonic acid (0.5 g) were added and the heating was continued at 160° C. overnight. The reaction mixture was cooled, the solvent was stripped and the residue was purified by column chromatography on silica gel eluting with ethyl acetate (100%) then ethanol/ethyl acetate (1/1), followed by recrystallization of the product from acetonitrile. Additional product was obtained by preparative thin layer chromatography of the mother liquors from the recrystallization steps eluting with ethyl acetate to afford a total of 0.6 g (14%) of 1-cyclopentyl-3-ethyl-6-[3-[2-(1-pyrrolidinyl)ethoxy]phenyl]pyrazolo[3,4-d]pyrimidin-4-one.

EXAMPLE 23

(a)

To a mixture of 3-hydroxybenzaldehyde (5.44 g, 44.55 mmol), K₂CO₃ (13.6 g) and DMF (50 ml) was added in portions 2-dimethylaminoethylchloride hydrochloride (7.1 g). The reaction mixture was stirred at room temperature overnight, filtered and the filtrate was stripped. The residue was diluted with 1N HCl (300 ml), and extracted with ether, and the ether layer was dried over MgSO₄ and stripped. The acidic aqueous layer was cooled and then treated with 8N NaOH till basic, then it was extracted with ether (3×150 ml). The ether layers were combined, dried over MgSO₄, filtered and stripped to afford, as an oily liquid, 1.43 g of 3-[2-(dimethylamino)ethoxy]benzaldehyde.

(b)+(c)

A mixture of 1-cyclopentyl-3-ethyl-5-amino-1H-pyrazole-4-carboxamide (3.50 g, 15.74 mmol), 3-[2-(dimethylamino)ethoxy]benzaldehyde (3.95 g) and xylenes (10 ml) was heated at 160° C. overnight. The reaction mixture was cooled to room temperature, the solvent was stripped, and the residue was partitioned between chloroform and water. The layers were separated, and the aqueous layer was extracted with chloroform. The organic layers were combined, washed with brine, dried over MgSO₄, filtered and stripped to afford, as an oil, 1-cyclopentyl-3- ethyl-6-[3-[2-(dimethylamino)ethoxy]phenyl]pyrazolo[3,4-d]pyrimidin-4-one labelled as [Example 23 (b)]. The free base was treated with ethanolic HCl to afford the product as the hydrochloride salt [labelled as Example 23 (c)].

EXAMPLE 24

(a)

A mixture of 3-fluorobenzonitrile (18 ml, 168.38 mmol), imidazole (11.46 g), $K_2CO_3$ (25.59 g), copper (1.75 g), potassium iodide (1.75 g) and DMF (125 ml) was refluxed overnight. The reaction mixture was cooled to room temperature and poured into ice/water (600 ml). A precipitate formed, which was collected by filtration, washed with water, dissolved in ethanol (25 ml)/$CHCl_3$ (500 ml) and filtered. The filtrates were partitioned in water, the organic layer was separated, dried over $MgSO_4$ and stripped. The residue was combined with the product from another experimental run and was recrystallized from $CHCl_3$/hexanes to afford 13.4 g of 3-(1-imidazolyl)benzonitrile.

(b)

To a mixture of 3-(1-imidazolyl)benzonitrile (3.16 g), 1-cyclopentyl-3-ethyl-5-amino-1H-pyrazole-4-carboxamide (3.77 g, 16.98 mmol) and DMF (75 ml) was added NaH (0.78 g, 60% dispersion in mineral oil). The reaction mixture was stirred at room temperature for about 2 days, then additional nitrile (0.1 equivalents) and NaH (0.2 equivalents) were added and the mixture was stirred at room temperature overnight. The solvent was stripped, and the residue was partitioned between chloroform (150 ml) and water (350 ml). The layers were separated, the aqueous layer was extracted with chlorform (2×100 ml), and the organic layers were combined, washed with brine, dried over $MgSO_4$, filtered and stripped. The product was dissolved in hot tert-butyldimethyl ether, filtered and stripped. The residue was treated with $CH_3CN$ and the solid which formed was collected by filtration to afford 2.10 g of 1-cyclopentyl-3-ethyl-6-[3-(1-imidazolyl)phenyl]pyrazolo[3,4-d]pyrimidin-4-amine.

(c)

To a solution of 1-cyclopentyl-3-ethyl-6-[3-(1-imidazolyl)phenyl]pyrazolo[3,4-d]pyrimidin-4-amine (6.24 g, 16.7 mmol), in 45 ml of $H_2O/H_2SO_4$ (1:1) in an EtOH/ice bath was added sodium nitrite (5.77 g) in water (5 ml) in small portions over 1.5 hours. The reaction mixture was warmed to room temperature and stirred overnight. The reaction mixture was poured into ice/water (500 ml) and neutralized with $NH_4OH$ to afford a yellow precipitate which was collected by filtration, washed with water, then ether. The product was recrystallized from EtOAc/MeOH, then MeOH to afford 1-cyclopentyl-3-ethyl-6-[3-(1-imidazolyl)phenyl]pyrazolo[3,4-d]pyrimidin-4-one, m.p. 264–265° C.

EXAMPLE 25

(a)

To a mixture of 3,4-dihydroxybenzaldehyde (3.46 g, 25.05 mmol), $K_2CO_3$ (11.08 g) and DMF (50 ml) which was stirred at room temperature for 1 hour, was added N-(2-chloroethyl)morpholine hydrochloride (9.79 g). The reaction mixture was stirred at room temperature overnight, then on a steam bath for 6 hours. Starting material was still present so additional $K_2CO_3$ (1.73 g) and N-(2-chloroethyl) morpholine hydrochloride (4.66 g) were added and the mixture was heated on a steam bath overnight. The reaction mixture was filtered, the filtrate was stripped and the residue was taken up in 2N HCl (200 ml) and partitioned with $CHCl_3$ (100 ml). The aqueous layer was extracted with $CHCl_3$ (2×150 ml), and the organic layers were combined. The aqueous layer was chilled, then treated with concentrated $NH_4OH$ until neutral. The aqueous layer was then extracted with $CHCl_3$ (3×150 ml), and the organic layers were combined, washed with brine, dried over $MgSO_4$, filtered and stripped to afford 3,4-[2-(4-morpholinyl)ethoxy]benzaldehyde.

(b)

A mixture of 1-cyclopentyl-3-ethyl-5-amino-1H-pyrazole-4-carboxamide (2.09 g, 9.4 mmol), 3,4-[2-(4-morpholinyl)ethoxy]benzaldehyde (5.14 g) and xylenes (25 ml) was heated at 160° C. for about 2 days. Starting material was still present so p-toluenesulfonic acid (6.0 g) was added and the mixture was heated at 160° C. overnight. The reaction mixture was cooled to room temperature, water and methanol were added and the mixture was stripped to afford an oily residue. The residue was partitioned between 1N NaOH (300 ml) and EtOAc (100 ml), the layers were separated, and the aqueous layer was extracted with EtOAc (1×150 ml). The organic layers were combined, washed with brine, dried over $MgSO_4$, filtered and stripped. The solid product was recrystallized from EtOAc to afford 1.51 g of 1-cyclopentyl-3-ethyl-6-[3,4-[2-(4-morpholinyl)ethoxy]phenyl]pyrazolo[3,4-d]pyrimidin-4-one.

EXAMPLE 26

(a)

To a mixture of ethyl 2-hydroxybenzoate (2.4 ml, 16.38 mmol), $K_2CO_3$ (4.98 g), and DMF (30 ml) was added N-(3-chloropropyl)morpholine hydrochloride (3.93 g). The mixture was stirred at room temperature for 30 minutes, then was warmed on a steam bath overnight. The reaction mixture was cooled, filtered and stripped to afford a liquid which was partitioned between EtOAc (350 ml) and water. The organic layer was separated, washed with water (2×200 ml), dried over $MgSO_4$ and stripped to afford ethyl 2-[3-(4-morpholinyl)propoxy]benzoate.

(b)+(c)

Sodium spheres (0.42 g) were dissolved in ethanol (20 ml) and then 1-cyclopentyl-3-ethyl-5-amino-1H-pyrazole-4-carboxamide (2.02 g, 9.10 mmol) was added, followed by ethyl 2-[3-(4-morpholinyl)propoxy]benzoate (5.33 g). The reaction mixture was refluxed for 3 days, then stirred at room temperature, and then the solvent was stripped. The residue was dissolved in water (250 ml), acidified to a pH of about 7 with acetic acid and extracted with $CHCl_3$. The organic layers were washed with brine, dried over $MgSO_4$ and stripped to afford an oil. The oil was taken up in ether, filtered and the filtrate was stripped and purified by column chromatography on silica eluting with EtOAc (100%) followed by EtOAc/MeOH (80/20) to afford 2.71 g of 1-cyclopentyl-3-ethyl-6-[2-[3-(4-morpholinyl)propoxy]phenyl]pyrazolo[3,4-d]pyrimidin-4-one, as a liquid [labelled as Example 26 (b)]. The free base was treated with EtOH.HCl and 1.14 g of the hydrochloride salt (labelled as Example 26 (c)) was obtained, m.p. 220–221° C.

EXAMPLE 27

(a)

To a stirred solution of KOH (5.81 g) in DMSO (15 mL) was added imidazole (5.0 g, 73.4 mmol). The mixture was stirred for 1 hour, then 2-fluorobenzonitrile (8.76 mL) in DMSO (10 mL) was added dropwise over 20 minutes. The reaction mixture was stirred at room temperature overnight and the product was collected by filtration and washed with water to afford 10.91 g of 2-(1-imidazolyl)benzonitrile as a white solid.

(b)

To a mixture of 2-(1-imidazolyl)benzonitrile (3.14 g), 1-cyclopentyl-3-ethyl-5-amino-1H-pyrazole-4-carboxamide (3.75 g, 16.59 mmol) and DMF (75 ml) was added 60% NaH (0.78 g, 60% dispersion in mineral oil). The reaction mixture was stirred at room temperature overnight, poured into ice/water (600 ml) and treated with acetic acid until a pH of 7 was obtained. The product was collected by filtration, and recrystallized from EtOAc/hexane to afford 2.82 g of 1-cyclopentyl-3-ethyl-6-[2-(1-imidazolyl)phenyl]pyrazolo[3,4-d]pyrimidin-4-amine.¼ hydrate.

(c)

To a solution of 1-cyclopentyl-3-ethyl-6-[2-(1-imidazolyl)phenyl]pyrazolo[3,4-d]pyrimidin-4-amine ¼ hydrate (2.55 g, 6.837 mmol) in 35 ml of $H_2O/H_2SO_4$ (1/1) in an EtOH/ice bath was added dropwise $NaNO_2$ (2.36 g) in water (10 ml) over 2 hours. The reaction mixture was stirred ovenight, poured into ice water (750 ml) and neutralized with $NH_4OH$. A precipitate formed which was collected by filtration, and washed with water, then ether to afford 0.75 g of the product. An additional 1.74 g of product was extracted from the filtrate and these combined product fractions were recrystallized from EtOAc, and then were dissolved in chloroform and stripped to afford, as a white powder, 1.42 g of 1-cyclopentyl-3-ethyl-6-[2-(1-imidazolyl)phenyl]pyrazolo[3,4-d]pyrimidin-4-one, m.p. 192–194° C.

EXAMPLE 28

A mixture of 1-cyclopentyl-3-ethyl-5-amino-1H-pyrazole-4-carboxamide (2.0 g, 9 mmol), 4-nitrobenzaldehyde (2.04 g, 13.5 mmol), methanesulfonic acid (0.25 ml) and xylenes (50 ml) was heated at reflux overnight, followed by an additional 6 hours. Ethanol (200 ml) was added to the reaction mixture, which was then refluxed and then treated with DARCO®. The reaction mixture was filtered, concentrated to 100 ml and then cooled. Yellow needles formed, which were collected by filtration and washed with ether to afford 0.53 g (17%) of 1-cyclopentyl-3-ethyl-6-(4-nitrophenyl)pyrazolo[3,4-d]pyrimidin-4-one, m.p. 321–323° C. (dec.).

EXAMPLE 29

(a)

To a mixture of 1-cyclopentyl-3-ethyl-5-amino-1H-pyrazole-4-carboxamide (5.0 g, 22.5 mmol), ethyl 4-chloro-2-ethoxybenzoate (5.4 g, 23.6 mmol) and DMF (50 ml) cooled in an ice bath was added NaH (3.9 g, 97.5 mmol, 60% dispersion in mineral oil). The reaction mixture was stirred in the ice bath for 2 hours, then at room temperature overnight. The reaction mixture was then concentrated in vacuo, and the residue was treated with water (100 ml) and acidified with acetic acid. The mixture was extracted with $CHCl_3$ (2×150 ml), the organic layers were concentrated in vacuo and the oily residue was crystallized from ether. The product was collected by filtration and dried. Recrystallization of the product from isopropanol/ether afforded 6.2 g of 1-cyclopentyl-3-ethyl-5-(4-chloro-2-ethoxyphenylcarboxamido)-1H-pyrazole-4-carboxamide, m.p. 175–177° C.

(b)

A mixture of 1-cyclopentyl-3-ethyl-5-(4-chloro-2-ethoxyphenylcarboxamido)-1H-pyrazole-4-carboxamide (1.0 g, 2.11 mmol) and N-methyl-2-pyrrolidinone (3 ml) was heated at 185–190° C. for 6 hours. The reaction mixture was cooled to room temperature, and treated with water (25 ml) and the product was collected by filtration and recrystallized from isopropanol to afford 1-cyclopentyl-3-ethyl-6-(4-chloro-2-ethoxyphenyl)pyrazolo[3,4-d]pyrimidin-4-one, m.p. 185–187° C.

EXAMPLE 30

A mixture of 1-cyclopentyl-3-ethyl-5-(4-chloro-2-ethoxyphenylcarboxamido)-1H-pyrazole-4-carboxamide (4 g, 9.8 mmol), imidazole (5.0 g, 73.5 mmol), KF (4.5 g, 77.5 mmol) and N-methyl-2-pyrrolidinone (10 ml) was heated at 185–190° C. for 2.5 hours, then at room temperature overnight. Water (20 ml) was added to the reaction mixture, and the mixture was acidified with acetic acid. A precipitate formed which was collected by filtration, washed with water and dried to afford 2.8 g of 1-cyclopentyl-3-ethyl-6-(4-chloro-2-hydroxyphenyl)pyrazolo[3,4-d]pyrimidin-4-one, as white needles, m.p. >300° C.

EXAMPLE 31

To a mixture of 1-cyclopentyl-3-ethyl-6-(4-nitrophenyl)pyrazolo[3,4-d]pyrimidin-4-one (1.38 g, 3.9 mmol), $SnCl_2.2H_2O$ (2.64 g, 11.72 mmol), ethanol (24 ml) and water (10 ml) was added concentrated HCl (14.5 ml). The reaction mixture was refluxed for 2 hours, cooled, and the product was collected by filtration and dried in vacuo to afford 0.85 g (67%) of 1-cyclopentyl-3-ethyl-6-(4-aminophenyl)pyrazolo[3,4-d]pyrimidin-4-one hydrochloride ⅓ hydrate, m.p. 279° C. (dec.).

EXAMPLE 32

A mixture of 1-cyclopentyl-3-ethyl-5-amino-1H-pyrazole-4-carboxamide (2.0 g, 9.0 mmol), 2,3-dihydrobenzo[b]furan-5-carboxaldehyde (1.73 g, 11.7 mmol), methanesulfonic acid (0.25 ml) and xylenes (50 ml) was refluxed for 20 hours and then allowed to stand for about 2 days. The reaction mixture was diluted with ether and the product was collected by filtration and dried to afford 1.65 g (52%) of 1-cyclopentyl-3-ethyl-6-(2,3-dihydrobenzo[b]furan-5-yl)pyrazolo[3,4-d]pyrimidin-4-one ¹⁄₁₀ hydrate, m.p. 253–254° C.

EXAMPLE 33

To a mixture of 1-cyclopentyl-3-ethyl-6-(4-aminophenyl)pyrazolo[3,4-d]pyrimidin-4-one hydrochloride ⅓ hydrate (0.61 g, 1.7 mmol) in dry pyridine (20 ml) in an ice bath was added methanesulfonyl chloride (0.49 g, 4.25 mmol). The reaction mixture was stirred at room temperature for about two days, the solvent was stripped to dryness and the residue was treated with water. The product was collected by filtration and recrystallized from ethanol, after DARCO® treatment, to afford 0.49 g (72%) of 1-cyclopentyl-3-ethyl-6-[4-(methylsulfonylamino)phenyl]pyrazolo[3,4-d]pyrimidin-4-one, m.p. 325° C. (dec.).

EXAMPLE 34

(a)

To a solution of 2-hydroxybenzaldehyde (6.11 g, 0.05 mol) in DMF (50 ml) under argon in an ice bath was added NaH (2.0 g, 0.05 mol, 60% dispersion in mineral oil), followed 1 hour later by 2-chloroethylmethyl ether (4.73 g, 0.05 mol). The reaction mixture was allowed to stand for about 2 days, then was heated at 70° C. for 7 hours. The reaction mixture was stripped to dryness, the residue was partitioned between water and $CHCl_3$, the layers were separated and the aqueous layer was extracted with $CHCl_3$ (2×75 ml). The product appeared to be in both layers, thus they were concentrated in vacuo and the residue was purified by column chromatography on silica gel eluting with ether to afford 1.5 g of 2-[2-(methoxy)ethoxy]benzaldehyde.

(b)

A mixture of 1-cyclopentyl-3-ethyl-5-amino-1H-pyrazole-4-carboxamide (1.07 g, 4.8 mmol), 2-[2-(methoxy)ethoxy]benzaldehyde (1.31 g, 7.2 mmol), xylenes (40 ml) and methanesulfonic acid (0.25 ml) was refluxed overnight. The reaction mixture was stripped to dryness, the residue was partitioned between $CH_2Cl_2$ and water, the layers were separated and the aqueous layer was extracted with $CH_2Cl_2$ (2×100 ml). The organic layers were combined, concentrated in vacuo and combined with silica gel (30 g). The preloaded silica gel was placed on a silica gel column and eluted with hexane/ether (1/1) to afford, after crystallization from hexane/tert-butylmethyl ether (25/1), 0.305 g (17%) of 1-cyclopentyl-3-ethyl-6-[2-[2-(methoxy)ethoxy]phenyl]pyrazolo[3 4-d]pyrimidin-4-one, m.p. 71–72° C.

EXAMPLE 35

(a)

To a solution of 3-hydroxy-4-methoxybenzaldehyde (8.56 g, 56.26 mmol) in $CH_3CN$ (50 ml) was added $K_2CO_3$ (17.1 g) with $CH_3CN$ (20 ml), followed 20 minutes later by N-(2-chloroethyl)morpholine hydrochloride (11.52 g). The reaction mixture was refluxed overnight, and then was cooled to room temperature, filtered, and the solvent was stripped to give, as an amber oil, 4-methoxy-3-[2-(4-morpholinyl)ethoxy]benzaldehyde.

(b)

A mixture of 1-cyclopentyl-3-ethyl-5-amino-1H-pyrazole-4-carboxamide (1.25 g, 5.63 mmol), 4-methoxy-3-[2-(4-morpholinyl)ethoxy]benzaldehyde (1.64 g), and xylenes (12 ml) was heated at 160° C. overnight. Additional aldehyde (0.5 g) was added and the mixture was refluxed until complete, then cooled to room temperature. The solvent was stripped, the residue was slurried with EtOAc and the product was collected by filtration and combined with the product from a similar experimental run. The combined product was recrystallized from $CH_3CN$ to afford 1-cyclopentyl-3-ethyl-6-[4-methoxy-3-[2-(4-morpholinyl)ethoxy]phenyl]pyrazolo[3,4-d]pyrimidin-4-one, m.p. 205–206° C.

EXAMPLE 36

1-cyclopentyl-3-ethyl-6-[2-($CH_2$=CH—$CH_2$O)phenyl]pyrazolo[3,4-d]pyrimidin-4-one (5.84 g) was heated at 210° C. for 2 hours. Ether was added and the mixture was filtered and the product was recrystallized from ethanol, then DMF to afford 3.42 g of 1-cyclopentyl-3-ethyl-6-[2-hydroxy-3-(2-propenyl)phenyl]pyrazolo[3,4-d]pyrimidin-4-one, m.p. >280° C.

EXAMPLE 37

(a)

To a mixture of 2-hydroxy-4-(diethylamino)benzaldehyde (10.0 g, 51.75 mmol), $K_2CO_3$ (14.3 g) and DMF (150 ml) at room temperature was added ethyl iodide (4.1 ml). The reaction mixture as stirred for about two days, filtered and the filtrate was concentrated in vacuo. The residue was partitioned between ether and saturated $Na_2CO_3$, and the organic layer was separated, dried over MgSO4, treated with charcoal, filtered and concentrated in vacuo. The solid product was recrystallized from hexane to afford, as a pink crystalline solid, 9.8 g of 2-ethoxy-4-(diethylamino)benzaldehyde, m.p. 58–59° C.

(b)

A mixture of 2-ethoxy-4-(diethylamino)benzaldehyde (7.87 g, 35.56 mmol), 1-cyclopentyl-3-ethyl-5-amino-1H-pyrazole-4-carboxamide (3.95 g, 17.78 mmol), p-toluenesulfonic acid monohydrate (0.05 g), 10% palladium on carbon (0.11 g) and benzene (150 ml) was refluxed overnight with the azeotropic removal of water. The catalyst was removed by filtration, and the filtrate was concentrated in vacuo. The residue was combined with that from a similar experimental run, and dissolved in $CH_2Cl_2$, and loaded onto a silica gel column. Elution of the column with ether/hexane (60/40) afforded a green foam which was titurated with refluxing hexane, and cooled and the product, as pale yellow needles, was collected by filtration to afford 1.19 g (8%) of 1-cyclopentyl-3-ethyl-6-[2-ethoxy-4-(diethylamino)phenyl]pyrazolo[3,4-d]pyrimidin-4-one, m.p. 138–139° C.

EXAMPLE 38

(a)

To a suspension of $K_2CO_3$ (82.88 g, 0.6 mol) in $CH_3CN$ (300 ml) was added 3,5-dihydroxybenzoic acid (4.62 g, 0.03 mol), followed 10 minutes later by N-(2-chloroethyl)morpholine hydrochloride (18.42 g, 0.099 mol). The reaction mixture was refluxed overnight, cooled, filtered and the filtrate was concentrated in vacuo. The oily residue was purified by column chromatography on silica gel eluting with acetone, followed by Kugelrohr distillation at >195° C. and 0.2 mm Hg to afford 7.45 g of 4-morpholinylethyl 3,5-di-[2-(4-morpholinyl)ethoxy]benzoate.

(b)

A mixture of 4-morpholinylethyl 3,5-di-[2-(4-morpholinyl)ethoxy]benzoate (2.0 g, 4 mmol), 1-cyclopentyl-3-ethyl-5-amino-1H-pyrazole-4-carboxamide (0.45 g, 2 mmol), $NaOCH_3$ (0.23 g, 4 mmol) and ethanol (50 ml) was refluxed for 96 hours. The reaction was incomplete so an additional equivalent of the benzoate and $NaOCH_3$ were added and the mixture was reluxed for 48 hours. The reaction mixture was stripped to dryness, and the residue was treated with water and acidified with acetic acid. The mixture was cooled and the product was isolated by filtration and dried at 90° C. to afford 0.61 g (54%) of 1-cyclopentyl-3-ethyl-6-[3,5-di[2-(4-morpholinyl)ethoxy]phenyl]pyrazolo[3,4-d]pyrimidin-4-one, m.p. 182–183° C.

EXAMPLE 39

To a suspension of 1-cyclopentyl-3-ethyl-6-[2-hydroxy-3-(2-propenyl)phenyl]pyrazolo[3,4-d]pyrimidin-4-one (1.0 g) in acetic acid (15 ml) was added sulfuric acid (15 ml) while cooling in an ice bath. The reaction mixture was warmed to room temperature and stirred overnight. The reaction mixture was poured into ice/water, a precipitate formed which was collected by filtration and washed with water. The product was purified by recrystallization from ether, followed by column chromatography on silica gel eluting with 25% EtOAc/hexane to afford 0.5 g of 1-cyclopentyl-3-ethyl-6-[2-methyl-2,3-dihydrobenzo[b]furan-5-yl]pyrazolo[3,4-d]pyrimidin-4-one, m.p. 164–165° C.

EXAMPLE 40

(a)

3-(Ethoxycarbonylmethoxy)benzaldehyde (9.55 g, 45.91 mmol) was dissolved in ethanol (75 ml) and water (25 ml) and then KOH (3.02 g) was added. The reaction mixture was stirred at room temperature until the reaction was complete and then the product was collected by filtration and dried to afford, as a white powder, 3.78 g of the potassium salt of 3-(carboxymethoxy)benzaldehyde.

(b)

The potassium salt of 3-(carboxymethoxy)benzaldehyde was dissolved in water and treated with 9N $HNO_3$. A precipitate formed which was collected by filtration, washed with water and dried at 75° C. under high vacuum to afford 1.66 g of 3-(carboxymethoxy)benzaldehyde.

(c)

3-(Carboxymethoxy)benzaldehyde (1.63 g, 9.05 mmol) was dissolved in p-dioxane (20 ml) and cooled in an ice bath and then N,N'-carbonyldiimidazole (1.9 g) was added in one portion. The reaction mixture was stirred for 30 minutes, then morpholine (0.8 ml) was added and the mixture was warmed to room temperature and stirred until the reaction was complete. The solvent was removed in vacuo, the residue was partitioned between $CHCl_3$ (100 ml) and 2N HCl (75 ml), the layers were separated, and the aqueous layer was extracted with $CHCl_3$ (2×75 ml). The organic layers were combined, dried over $MgSO_4$ and stripped to afford an oil which was combined with the product from a similar experimental run and purified by column chromatography on silica gel eluting with chloroform to afford 2.1 g of 3-[4-morpholinylcarbonylmethoxy]benzaldehyde.

(d)

A mixture of 1-cyclopentyl-3-ethyl-5-amino-1H-pyrazole-4-carboxamide (1.87 g), 3-[4-morpholinylcarbonylmethoxy]benzaldehyde (2.1 g, 8.43 mmol) and xylenes (20 ml) was heated at 160° C. for about 2 days. The solvent was removed, then methanol was added to the residue and the product was collected by filtration. Additional product was obtained from the filtrates and the product fractions were pooled and recrystallized from $CH_3CN/CHCl_3$ to afford 1-cyclopentyl-3-ethyl-6-[3-(4-morpholinylcarbonylmethoxy)phenyl]pyrazolo[3,4-d]pyrimidin-4-one, m.p. 212–213° C.

EXAMPLE 41

(a)

A mixture of 3-hydroxybenzaldehyde (5.17 g, 42.33 mmol), $K_2CO_3$ (58.5 g) and $CH_3CN$ (100 ml) was stirred at room temperature for 15 minutes, then dibromoethane (18.3 ml) was added. The reaction mixture was stirred at room temperature for 30 minutes, then at reflux for 3–4 hours. Additional dibromoethane was added and then the reaction mixture was refluxed overnight. The reaction mixture was cooled, filtered, and the filtrate was stripped to afford an oil. The oil was dissolved in ether (300 ml), washed with 5N NaOH (2×75 ml) and the ether layer was dried over $MgSO_4$ and stripped. The residue was purified by column chromatography on silica gel eluting with 10% ethyl acetate/hexane to afford 5.23 g of 3-(2-bromoethoxy)benzaldehyde.

(b)

A mixture of 3-(2-bromoethoxy)benzaldehyde (3.91 g, 17.07 mmol), $K_2CO_3$ (3.1 g), thiomorpholine (1.9 ml) and DMF (30 ml) was warmed on a steambath overnight. Additional $K_2CO_3$ (0.7 g) and thiomorpholine (1.0 ml) were added and the reaction mixture was warmed on a steam bath overnight. The reaction mixture was cooled to room temperature, filtered and the filtrate was stripped to afford an amber oil. The oil was combined with the product from a similar experimental run and purified by column chromatography on silica gel eluting with EtOAc (100%) to afford, as an oil, 3-[2-(4-thiomorpholinyl)ethoxy]benzaldehyde.

(c)

A mixture of 3-[2-(4-thiomorpholinyl)ethoxy]benzaldehyde (3.2 g, 12.75 mmol), 1-cyclopentyl-3-ethyl-5-amino-1H-pyrazole-4-carboxamide (2.55 g) and xylenes (20 ml) was heated at 160° C. overnight. The reaction mixture was cooled in an ice bath, and then the solvent was removed to afford an oil which crystallized on standing. The product was treated with hot $MeOH/Et_2O$, the mixture was cooled, and the product was collected by filtration and washed with ether to afford 0.51 g of desired product. The filtrate was concentrated in vacuo to afford 5.0 g of the 6,7-dihydro derivative which was dissolved in xylenes (25 ml), treated with palladium on carbon and heated at 110° C. for 3 hours. Additional palladium on carbon (1.5 g) was added and heating was continued for 2 hours. The mixture was filtered through CELITE® and the filtrate was stripped. The residue was treated with methanol and the product was collected by filtration and combined with the 0.51 g of product obtained above and the product obtained from a similar experimental run. The combined product fractions were recrystallized from EtOAc, washed with ether and dried at 100° C. under high vacuum to afford 1-cyclopentyl-3-ethyl-6-[3-[2-(4-thiomorpholinyl)ethoxy]phenyl]pyrazolo[3,4-d]pyrimidin-4-one.

EXAMPLE 42

(a)

To a mixture of 3-hydroxybenzonitrile (4.76 g, 0.04 mol), $K_2CO_3$ (16.6 g, 0.12 mol) and DMF (100 ml) under argon was added 4-chloromethylpyridine hydrochloride (6.56 g, 0.04 mol). The reaction mixture was stirred at room temperature for about two days, the solvent was evaporated and the residue was partitioned between water and $CH_2Cl_2$. The organic layer was washed with 2N aqueous NaOH (1×100 ml), brine, then was dried over $MgSO_4$. The solvent was removed in vacuo to afford, as an amber solid, 9.0 g of 3-(4-pyridinylmethoxy)benzonitrile.

(b)

A mixture of 3-(4-pyridinylmethoxy)benzonitrile (2.5 g, 0.012 mol) in 75% formic acid (35 ml) was treated with raney nickel (2 g) and heated to reflux for 4 hours. The reaction mixture was filtered through SUPERCELL®, the filtrate was brought to a pH of 8–9 with 5N NaOH, extracted with EtOAc (3×150 ml) and the combined organic layers were dried over $MgSO_4$, filtered and stripped. The residue was purified by column chromatography on silica gel eluting with EtOAc (100%) to afford 0.94 g (37%) of 3-(4-pyridinylmethoxy)benzaldehyde.

(c)

A mixture of 1-cyclopentyl-3-ethyl-5-amino-1H-pyrazole-4-carboxamide (2.7 g, 0.124 mol), 3-(4-pyridinylmethoxy)benzaldehyde (3.95 g, 0.0185 mol) and xylenes (100 ml) was refluxed overnight. Additional carboxamide (1 g) was added and the mixture was refluxed for another 2 days. 10% palladium on carbon (1 g) was added and the mixture was refluxed for another 3 hours. The catalyst was removed by filtration, the filtrate was concentrated in vacuo and the solid residue was collected by filtration. Additional product was obtained by concentration of the mother liquors and the combined product fractions were recrystallized from ethyl acetate to afford 1.66 g of 1-cyclopentyl-3-ethyl-6-[3-[4-pyridinylmethoxy]phenyl]pyrazolo[3,4-d]pyrimidin-4-one, m.p. 230–232° C.

EXAMPLE 43

(a)

A mixture of 3-hydroxybenzaldehyde (3.66 g, 0.03 mol), $K_2CO_3$ (12.43 g, 0.09 mol), and $CH_3CN$ (100 ml) was stirred at room temperature for ½ hour, then N-methyl-2-chloromethylpiperidine hydrochloride (5.49 g, 0.03 mol) was added. The reaction mixture was stirred until the reaction was complete, then the solvent was removed in vacuo and the residue was partitioned between $CHCl_3$ and water. The aqueous layer was extracted with $CHCl_3$ (3×100 ml) and the combined organic layers were concentrated in vacuo to afford 3-(1-methyl-3-hexahydroazepinyloxy)benzaldehyde.

(b)

A mixture of 3-(1-methyl-3-hexahydroazepinyloxy)benzaldehyde (0.79 g, 3.4 mol), 1-cyclopentyl-3-ethyl-5-amino-1H-pyrazole-4-carboxamide (0.5 g, 2.2 mmol), methanesulfonic acid (0.25 ml) and xylenes (25 ml) was refluxed overnight. The solvent was stripped, the residue was dissolved in $CH_2Cl_2$ and purified by column chromatography on silica gel eluting with ether, then acetone, then 0.5% $Et_3N$/acetone to afford 0.43 g (45%) of 1-cyclopentyl-3-ethyl-6-[3-(1-methyl-3-hexahydroazepinyloxy)phenyl]pyrazolo[3,4-d]pyrimidin-4-one, m.p. 195–196° C.

EXAMPLE 44

To a mixture of 1-cyclopentyl-3-ethyl-6-[3-[4-pyridinylmethoxy]phenyl]pyrazolo[3,4-d]pyrimidin-4-one (1.1 g) in acetic acid (100 ml)/water (50 ml) was added $Pt_2O$ (200 mg). The mixture was hydrogenated at 50 psi with heating (variac set at 40) for four hours. The catalyst was removed by filtration, the filtrate was concentrated and the residue was partitioned between $NH_4OH$ and ethyl acetate. The organic layer was separated, washed with brine, dried over $MgSO_4$, filtered and concentrated. The residue was purified by column chromatography on silica gel eluting with ethyl acetate, followed by preparative thin layer chromatography eluting with ethyl acetate to afford, after recrystallization from EtOAc, 64 mg of 1-cyclopentyl-3-ethyl-6-(3-hydroxyphenyl)pyrazolo[3,4-d]pyrimidin-4-one, m.p. 275–278° C. (dec.).

EXAMPLE 45

(a)

To a stirred solution of 3-hydroxybenzaldehyde (8 g, 65 mmol), 1-methyl-4-piperidinol (7.5 g, 65 mmol), triphenylphosphine (13.1 g, 65 mmol) and THF (100 ml) was added diethylazodicarboxylate (11.4 g, 65 mmol) in THF (20 ml) over a 35 minute period. The reaction mixture was stirred in an ice bath for 3 hours, then at room temperature for 5 days. The reaction mixture was concentrated in vacuo, and partitioned between $CHCl_3$ (300 ml) and 3N HCl (300 ml). The aqueous layer was concentrated in vacuo, the residue was treated with 10% $K_2CO_3$ and extracted with $CHCl_3$ (2×100 ml). The solvent was removed in vacuo to afford 7.4 g of crude 3-(1-methyl-4-piperidinyloxy)benzaldehyde.

(b)

A mixture of 3-(1-methyl-4-piperidinyloxy)benzaldehyde (7.4 g), 1-cyclopentyl-3-ethyl-5-amino-1H-pyrazole-4-carboxamide (2 g) and xylenes (200 ml) was refluxed for 31 hours and then was stirred at room temperature for several days. The solvent was removed in vacuo, and the residue was purified by column chromatography on silica gel eluting with ether (100%) to 10% methanol/ether to afford, after recrystallization from isopropanol, 2.3 g of 1-cyclopentyl-3-ethyl-6-[3-(1-methyl-4-piperidinyloxy)phenyl]pyrazolo[3,4-d]pyrimidin-4-one ¼ hydrate.

EXAMPLE 46

(a)

To a stirred solution of 2,4-difluorobenzonitrile (25 g, 0.18 mol) in p-dioxane (250 ml) in an ice-bath was added sodium ethoxide (15 g, 0.22 mol) over 45 minutes. The reaction mixture was stirred as such for 2 hours, then at room temperature for 18 hours. The solvent was concentrated in vacuo and the residue was partitioned between water (200 ml) and $CH_2Cl_2$ (400 ml) and acidified with acetic acid. The organic layer was separated, dried over $MgSO_4$ and concentrated in vacuo to afford, as a yellow oil, 26.7 g of a mixture of 2-ethoxy-4-fluorobenzonitrile and 4-ethoxy-2-fluorobenzonitrile.

(b)

To a mixture of the benzonitriles from Example 46 (a) (26.5 g, 0.16 mol), imidazole (11.5 g, 0.17 mol), and p-dioxane (150 ml) cooled in an ice bath was added NaH (6.8 g, 60% dispersion in mineral oil) over a 30 minute period. The reaction mixture was stirred for 1 hour as such, then at room temperature for 24 hours, followed by standing at room temperature for 24 hours. The solvent was removed in vacuo, the residue was partitioned between $CH_2Cl_2$ (2×300 ml) and water (100 ml). The $CH_2Cl_2$ extracts were combined, concentrated in vacuo and the residue was purified by column chromatography on silica eluting with ether (100%) to 10% methanol/ether to afford 10.1 g of 4-(1-imidazolyl)-2-ethoxybenzonitrile, m.p. 134–136° C.

(c)

A mixture of 1-cyclopentyl-3-ethyl-5-amino-1H-pyrazole-4-carboxamide (1.5 g, 6.3 mmol), 4-(1-imidazolyl)-2-ethoxybenzonitrile (1.5 g, 7 mmol), NaH (0.84 g, 21 mmol, 60% dispersion in mineral oil) and p-dioxane (75 ml) was heated on a steam bath for 12 hours, then was stirred at room temperature overnight. The reaction mixture was acidified with acetic acid, concentrated in vacuo, and water was added to the residue. A gummy solid formed which was collected, washed with water, dried and purified by column chromatography on silica gel eluting with ether (100%) to 15% methanol/ether to afford, after recrystallization from acetonitrile, 0.78 g (36%) of 1-cyclopentyl-3-ethyl-6-[4-(1-imidazolyl)-2-ethoxyphenyl] pyrazolo[3,4-d]pyrimidin-4-one, m.p. 204–206° C.

EXAMPLE 47

Following a procedure similar to that described in Example 1 (c), but substituting 1-tert-butyl-3-ethyl-5-amino-1H-pyrazole-4-carboxamide for 1-cyclopentyl-3-ethyl-5-amino-1H-pyrazole-4-carboxamide and 2,4,6-trimethylbenzaldehyde for 2-propoxybenzaldehyde, it is contemplated that there can be prepared 1-tert-butyl-3-ethyl-6-[2,4,6-trimethylphenyl]pyrazolo[3,4-d]pyrimidin-4-one.

EXAMPLE 48

Following procedures similar to those described in Examples 1 (b) and 1 (c), but substituting 1-cyclopentyl-3-phenylmethyl-5-amino-1H-pyrazole-4-carbonitrile for 1-cyclopentyl-3-ethyl-5-amino-1H-pyrazole-4-carbonitrile in part 1 (b), it is contemplated that there can be prepared:

(a)

1-Cyclopentyl-3-phenylmethyl-5-amino-1H-pyrazole-4-carboxamide (b)

Cyclopentyl-3-phenylmethyl-6-(2-propoxyphenyl)pyrazolo[3,4-d]pyrimidin-4-one

BIOLOGICAL TEST RESULTS

In standard biological test procedures, the compounds of Formula I have been found to possess c-GMP-PDE V (formerly named as c-GMP-PDE I) inhibitory activity and are thus useful in the treatment of heart failure and hypertension. The compounds of Formula I, in combination with nitrates, have also been found to be useful in reversing or reducing nitrate-induced tolerance and thus would be further useful in the treatment of angina pectoris, congestive heart disease and myocardial infarction.

Multiple isozymic forms of cyclic nucleotide phosphodiesterase (PDE) have been identified in mammalian cells. These isozymes hydrolyze cyclic adenosine monophosphate (cAMP) and/or cyclic guanosine monophosphate (cGMP) to the presumably biologically inactive 5'-nucleotide phosphates. Elevation of intracellular cGMP in vascular smooth muscle triggers a cascade of events that leads to a reduction in muscle tone while elevations in renal tubule cell cGMP stimulates natriuresis and diuresis. Vascular smooth muscle and renal cells contain a phosphodiesterase isozyme that has a low Km (1 $\mu$M) for the hydrolysis of cGMP. This isozyme has been referred to as the cGMP-PDE or cGMP-PDE V (formerly named as cGMP-PDE I since it eluted from an anion-exchange sepharose resin in the first peak of PDE activity at a sodium acetate concentration between 150–200 mM). Thus inhibition of the cGMP-PDE isozyme is a viable subcellular mechanism by which increases in cGMP can produce a reduction in total peripheral resistance and a stimulation of natriuresis and diuresis. The development of cGMP-PDE inhibitors represents an approach for the discovery of agents useful for treating heart failure and hypertension. For example, compounds having high inhibitory potency for the cGMP-PDE are expected to lower blood pressure and induce natriuresis and diuresis.

The c-GMP-PDE V inhibitory activity of representative compounds of the invention was demonstrated by the following procedure.

The cGMP-PDE and other PDE isozymes were isolated from cardiovascular tissues (heart and aorta) of various animal species and man by anion-exchange and affinity chromatography as described by Silver et al., Sec. Messeng. Phos. 13:13–25, 1991; PDE activity, in the presence and absence of test compounds was determined essentially as described by Thompson et al., Adv. Cyclic Nucleotide Res. 10:69–92. To determine the potency and selectivity of compounds as PDE inhibitors, compounds are screened for their effect on cyclic nucleotide hydrolysis at 10 $\mu$M. If $\geq$50% inhibition of PDE activity is observed, an $IC_{50}$ value (concentration of compound causing 50% reduction in PDE activity) and corresponding 95% confidence intervals are generated. The $IC_{50}$ values are calculated from concentration-response curves as described by Tallarida and Murray, Manual of Pharmacologic Calculations with Computer Programs, Procedure 8, Graded Dose-response, pp. 14–19, Springer-Verlag, New York, 1981.

The following table summarizes the results obtained from the testing of representative compounds of the invention.

| Example No. | Percent Inhibition at Given $\mu$M or $IC_{50}$ (nM) cGMP-PDE V |
|---|---|
| 1(c) | 7/3* |
| 2 | 250 |
| 3 | 200 |
| 4 | 5.8 |
| 5 | 87 |
| 6 | 1.6 |
| 7 | 51% (10 $\mu$M) or 20% (1 $\mu$M) |
| 8(a) | 410/430* |
| 8(b) | 70% (1 $\mu$M) or 32% (0.1 $\mu$M) |
| 9(b) | 4.9 |
| 10 | 85% (10 $\mu$M) or 15% (1 $\mu$M) |
| 11(c) | 2700/4500* |
| 12(b) | 74% (1 $\mu$M) or 30% (0.1 $\mu$M) |
| 13(b) | 107 |
| 14 | 810 |
| 15 | 500 |
| 16 | 68% (10 $\mu$M) or 19% (1 $\mu$M) or 780 nM |
| 17(c) | 14% (0.1 $\mu$M) or 19% (1 $\mu$M) or 39% (10 $\mu$M) |
| 18(b) | 370 |
| 19(b) | 73 |
| 20(b) | 94 |
| 21 | 93 |
| 22(b) | 140 |
| 23(c) | 540 |
| 24(c) | 130 |
| 25(b) | 14/51* |
| 26(c) | 28% (1 $\mu$M) |
| 27(c) | 73% (1 $\mu$M) or 21% (0.1 $\mu$M) |
| 28 | 40% (1 $\mu$M) |
| 29(b) | 7.4/8.4* |
| 30 | 53% (1 $\mu$M) or 9% (0.1 $\mu$M) |
| 31 | 61% (1 $\mu$M) or 31% (0.1 $\mu$M) |
| 32 | 47% (1 $\mu$M) or 23% (0.1 $\mu$M) |
| 33 | 56% (1 $\mu$M) or 21% (0.1 $\mu$M) |
| 34(b) | 56% (0.1 $\mu$M) or 28% (0.01 $\mu$M) |
| 35(b) | 58% (0.1 $\mu$M) or 13% (0.01 $\mu$M) |
| 36 | 0% (0.1 $\mu$M) or 4% (1 $\mu$M) |
| 37(b) | 73% (1 $\mu$M) or 31% (0.1 $\mu$M) |
| 38(b) | 63% (0.1 $\mu$M) or 11% (0.01 $\mu$M) |
| 39 | 65% (0.1 $\mu$M) or 24% (0.01 $\mu$M) |
| 40(d) | 74% (1 $\mu$M) or 47% (0.1 $\mu$M) |
| 41(c) | 56% (1 $\mu$M) or 46% (0.1 $\mu$M) |
| 42(c) | 56% (0.1 $\mu$M) or 25% (0.01 $\mu$M) |
| 43(b) | 75% (1 $\mu$M) or 41% (0.1 $\mu$M) |
| 44 | 56% (1 $\mu$M) or 29% (0.1 $\mu$M) |
| 46(c) | 26% (0.1 $\mu$M) or 76% (1 $\mu$M) or 90% (10 $\mu$M) or 18 nM |

*The numbers represent $IC_{50}$ (nM) values for separate experimental runs.

The antihypertensive activity of representative compounds of the invention was demonstrated by the following procedure.

Spontaneously hypertensive rats (SHR) were anesthetized with sodium pentobarbital (50 mg/kg, ip) and instrumented with catheters positioned in the inferior vena cava and abdominal aorta for administration of drug and recording of arterial pressure and heart rate, respectively. After a 2 day recovery from surgery, three baseline blood pressure measurements were made at 5 min intervals in conscious SHR. Compounds to be tested or vehicle were then administered intravenously in a dose-dependent manner (0.3–10 mg base/kg) while arterial pressure was recorded continuously on a polygraph. The mean arterial pressure response was measured 5 minutes after the administration of each dose of the test compound and the next dose given in a cumulative dose fashion. The response to each dose of the test compound was calculated as the difference from the mean of the three baseline measurements.

The following table summarizes the results obtained from the testing of representative compounds of the invention.

| Example No. | SHR iv<br>% change in mean arterial pressure<br>at Given mg/kg or $ED_{25}$ (mg/kg) |
| --- | --- |
| 1(c) | −5% (1 mg/kg) |
| 3 | −7% (1 mg/kg) |
| 4 | −13% (10 mg/kg) |
| 5 | −8% (1 mg/kg) |
| 6 | −1% (10 mg/kg) |
| 8(a) | 5.7 or −35% (10 mg/kg) or<br>−20% (3 mg/kg) or −81% (30 mg/kg, po) |
| 9(b) | −19% (10 mg/kg) |
| 13(b) | 9.5 or −58% (30 mg/kg, po)<br>or −19% (3 mg/kg) or −14% (1 mg/kg)<br>or −11% (0.3 mg/kg) |
| 19(b) | 12.5 or −19% (10 mg/kg) |
| 21 | −1% (10 mg/kg) |
| 22(b) | 17.9 or −18% (10 mg/kg) |
| 24(c) | 12.7 or −21% (10 mg/kg) or −13% (3 mg/kg) |
| 25(b) | 4.5 or −38% (10 mg/kg) or<br>−27% (3 mg/kg) or −18% (1 mg/kg) or<br>−18% (10 mg/kg, po) |

The activity of representative compounds of the invention in reversing or reducing nitrate-induced tolerance was demonstrated by the following procedure:

Spontaneously hypertensive rats (17–25 weeks of age) were made nitroglycerin tolerant by repeated administration of high doses of nitroglycerin (100 mg/kg, s.c., 3 times/day for 3 consecutive days). To confirm tolerance challenge doses of nitroglycerin were administered intravenously at doses ranging from 1–300 μg/kg and the maximum change in mean arterial pressure (MAP) for each dose was recorded. Groups of tolerant rats were pretreated with the compounds of the invention (tolerant pretreated group) or with vehicle (0.05 N NaOH) (tolerant vehicle pretreated group) intravenously 5–10 minutes prior to administration of challenge doses of nitroglycerin. The administration of challenge doses of nitroglycerin to non-tolerant rats (the non-tolerant group) caused a dose-dependent decrease in MAP of between 10 to 40 mm Hg. The administration of challenge doses of nitroglycerin to the tolerant vehicle pretreated group resulted in a significant reduction of the hypotensive response. The administration of challenge doses of nitroglycerin to tolerant rats which were pretreated with the compounds of the invention (tolerant pretreated group) resulted in varying degrees of restoration of the hypotensive response. The area under the dose-MAP curve was calculated for the non-tolerant group and for the tolerant vehicle pretreated group and the tolerant pretreated group. The percent reversal of nitrate-induced tolerance was calculated as follows:

Percent Reversal=$(AUC_{tol\text{-}pretreated} - AUC_{tol\text{-}veh})/(AUC_{nontol} - AUC_{tol\text{-}veh}) \times 100$ wherein:

$AUC_{nontol}$=the area under the dose-MAP curve for the non-tolerant group.

$AUC_{tol\text{-}veh}$=the area under the dose-MAP curve for the tolerant vehicle pretreated group.

$AUC_{tol\text{-}pretreated}$=the area under the dose-MAP curve for the tolerant pretreated group.

A percent reversal of 100% or greater reflects complete reversal of nitrate-induced tolerance, whereas a percent reversal of 0% indicates that no reversal of nitrate-induced tolerance occurred. The following table summarizes the results obtained from the testing of representative compounds of the invention.

| Example | Dose (mg/kg) | Percent (%) Reversal of Nitroglycerin-induced Tolerance |
| --- | --- | --- |
| 6 | 1.0 | 49 |
| 8(a) | 0.3 | 5 |
| 13(b) | 0.3 | 58 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

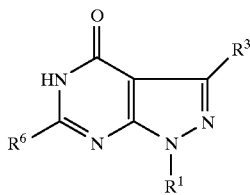

wherein:
$R^1$ is cyclopentyl;
$R^3$ is lower-alkyl, or phenyl-lower-alkyl; and
$R^6$ is phenyl, or phenyl substituted by from one to three, the same or different, substituents selected from the group consisting of lower-alkoxy, lower-alkyl, hydroxy, 1-imidazolyl, lower-alkenyloxy, dilower-alkylamino-lower-alkoxy, 4-morpholinyl-lower-alkoxy, lower-alkoxycarbonyl-lower-alkoxy, carboxylower-alkoxy, trifluoromethyl, 1-piperidinyl-lower-alkoxy, 1-pyrrolidinyl-lower-alkoxy, nitro, halo, amino, —$(CH_2)_2O$—, lower-alkylsulfonylamino, lower-alkoxy-lower-alkoxy, lower-alkenyl, dilower-alkylamino, —$OCH(CH_3)CH_2$—, 4-morpholinylcarbonyl-lower-alkoxy, 4-thiomorpholinyl-lower-alkoxy, pyridinyl-lower-alkoxy, 1-lower-alkyl-3-hexahydroazepinyloxy, and 1-lower-alkyl-4-piperidinyloxy; or a pharmaceutically acceptable acid-addition salt and/or hydrate thereof; with the proviso that when $R^1$ is cyclopentyl and $R^6$ is substituted phenyl at least one of the phenyl substituents must be selected from the group consisting of lower-alkoxy, lower-alkyl and halo.

2. A compound according to claim 1 wherein $R^1$ is cyclopentyl; and $R^3$ is lower-alkyl.

3. A compound according to claim 2 wherein $R^3$ is methyl or ethyl.

4. A compound according to claim 3 wherein $R^6$ is phenyl, or phenyl substituted by from one to two, the same or different, substituents selected from the group consisting of lower-alkoxy, lower-alkyl, hydroxy, 1-imidazolyl, lower-alkenyloxy, dilower-alkylamino-lower-alkoxy, 4-morpholinyl-lower-alkoxy, lower-alkoxycarbonyl-lower-alkoxy, carboxylower-alkoxy, trifluoromethyl, 1-piperidinyl-lower-alkoxy, 1-pyrrolidinyl-lower-alkoxy, nitro, halo, amino, —$(CH_2)_2O$—, lower-alkylsulfonylamino, lower-alkoxy-lower-alkoxy, lower-alkenyl, dilower-alkylamino, —$OCH(CH_3)CH_2$—, 4-morpholinylcarbonyl-lower-alkoxy, 4-thiomorpholinyl-lower-alkoxy, pyridinyl-lower-alkoxy, 1-lower-alkyl-3-hexahydroazepinyloxy, and 1-lower-alkyl-4-piperidinyloxy.

5. A compound according to claim 4 wherein $R^6$ is phenyl, or phenyl substituted by from one to two, the same or different, substituents selected from the group consisting of methoxy, ethoxy, propoxy, methyl, hydroxy, 1-imidazolyl, $CH_2$=$CHCH_2O$—, 2-(dimethylamino)ethoxy, 3-(dimethylamino)propoxy, 2-(4-morpholinyl)ethoxy, 3-(4-morpholinyl)propoxy, ethoxycarbonylmethoxy, carboxymethoxy, trifluoromethyl, 2-(1-piperidinyl)ethoxy, 2-(1-pyrrolidinyl)ethoxy, nitro, chloro, amino, —$(CH_2)_2O$—, methylsulfonylamino, 2-(methoxy)ethoxy, $CH_2$=$CH_2CH_2$—, diethylamino, —$OCH(CH_3)CH_2$—, 4-morpholinylcarbonylmethoxy, 2-(4-thiomorpholinyl)ethoxy, 4-pyridinylmethoxy, 1-methyl-3-hexahydroazepinyloxy, and 1-methyl-4-piperidinyloxy.

6. A compound according to claim 5 selected from the group consisting of:
1-cyclopentyl-3-ethyl-6-(2-propoxyphenyl)pyrazolo[3,4-d]pyrimidin-4-one,
1-cyclopentyl-3-ethyl-6-phenylpyrazolo[3,4-d]pyrimidin-4-one,
1-cyclopentyl-3-ethyl-6-[(2-methoxy-4-carboxymethoxy)phenyl]pyrazolo[3,4-d]pyrimidin-4-one,
1-cyclopentyl-3-ethyl-6-(4-chloro-2-hydroxyphenyl)pyrazolo[3,4-d]pyrimidin-4-one,
1-cyclopentyl-3-ethyl-6-[4-methoxy-3-[2-(4-morpholinyl)ethoxy]phenyl]pyrazolo[3,4-d]pyrimidin-4-one,
1-cyclopentyl-3-ethyl-6-[2-ethoxy-4-(diethylamino)phenyl]pyrazolo[3,4-d]pyrimidin-4-one, and
1-cyclopentyl-3-ethyl-6-[2-ethoxy-4-(1-imidazolyl)phenyl]pyrazolo[3,4-d]pyrimidin-4-one.

7. A pharmaceutical composition which comprises a compound according to claim 1 together with a pharmaceutically acceptable carrier, adjuvant, diluent, or vehicle.

8. A pharmaceutical composition which comprises a compound according to claim 2 together with a pharmaceutically acceptable carrier, adjuvant, diluent, or vehicle.

9. A pharmaceutical composition which comprises a compound according to claim 3 together with a pharmaceutically acceptable carrier, adjuvant, diluent, or vehicle.

10. A pharmaceutical composition which comprises a compound according to claim 4 together with a pharmaceutically acceptable carrier, adjuvant, diluent, or vehicle.

11. A pharmaceutical composition which comprises a compound according to claim 5 together with a pharmaceutically acceptable carrier, adjuvant, diluent, or vehicle.

12. A pharmaceutical composition which comprises a compound according to claim 6 together with a pharmaceutically acceptable carrier, adjuvant, diluent, or vehicle.

13. A method for effecting cGMP-phosphodiesterase inhibition in a mammalian organism which comprises administering to said organism an effective amount of a compound according to claim 1.

14. A method for effecting cGMP-phosphodiesterase inhibition in a mammalian organism which comprises administering to said organism an effective amount of a compound according to claim 2.

15. A method for effecting cGMP-phosphodiesterase inhibition in a mammalian organism which comprises administering to said organism an effective amount of a compound according to claim 3.

16. A method for effecting cGMP-phosphodiesterase inhibition in a mammalian organism which comprises administering to said organism an effective amount of a compound according to claim 4.

17. A method for effecting cGMP-phosphodiesterase inhibition in a mammalian organism which comprises administering to said organism an effective amount of a compound according to claim 5.

18. A method for effecting cGMP-phosphodiesterase inhibition in a mammalian organism which comprises administering to said organism an effective amount of a compound according to claim 6.

19. A method for treating heart failure and/or hypertension in a mammalian organism which comprises administering to said organism an effective amount of a compound according to claim 1.

20. A method for treating heart failure and/or hypertension in a mammalian organism which comprises administering to said organism an effective amount of a compound according to claim 2.

21. A method for treating heart failure and/or hypertension in a mammalian organism which comprises administering to said organism an effective amount of a compound according to claim 3.

22. A method for treating heart failure and/or hypertension in a mammalian organism which comprises administering to said organism an effective amount of a compound according to claim 4.

23. A method for treating heart failure and/or hypertension in a mammalian organism which comprises administering to said organism an effective amount of a compound according to claim 5.

24. A method for treating heart failure and/or hypertension in a mammalian organism which comprises administering to said organism an effective amount of a compound according to claim 6.

\* \* \* \* \*